(12) United States Patent
Wang et al.

(10) Patent No.: US 11,203,577 B2
(45) Date of Patent: Dec. 21, 2021

(54) SULFONYL-STRUCTURE-CONTAINING TRIAZINONE DERIVATIVES, THEIR PREPARATION METHODS AND THEIR USES IN INSECT KILLING AND/OR BACTERIUM KILLING

(71) Applicant: Nankai University, Tianjin (CN)

(72) Inventors: Qingmin Wang, Tianjin (CN); Hongjian Song, Tianjin (CN); Yan Yang, Tianjin (CN); Yuxiu Liu, Tianjin (CN); Ziwen Wang, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 770 days.

(21) Appl. No.: 16/073,214

(22) PCT Filed: Sep. 21, 2017

(86) PCT No.: PCT/CN2017/102600
§ 371 (c)(1),
(2) Date: Jul. 26, 2018

(87) PCT Pub. No.: WO2019/056246
PCT Pub. Date: Mar. 28, 2019

(65) Prior Publication Data
US 2021/0206731 A1    Jul. 8, 2021

(51) Int. Cl.
| | | |
|---|---|---|
| *C07D 403/12* | (2006.01) | |
| *C07D 413/12* | (2006.01) | |
| *C07D 405/12* | (2006.01) | |
| *C07D 401/14* | (2006.01) | |
| *A01N 43/707* | (2006.01) | |
| *A01N 43/80* | (2006.01) | |
| *C07D 253/06* | (2006.01) | |
| *C07D 409/12* | (2006.01) | |

(52) U.S. Cl.
CPC ......... *C07D 253/06* (2013.01); *A01N 43/707* (2013.01); *A01N 43/80* (2013.01); *C07D 401/14* (2013.01); *C07D 403/12* (2013.01); *C07D 405/12* (2013.01); *C07D 409/12* (2013.01); *C07D 413/12* (2013.01)

(58) Field of Classification Search
None
See application file for complete search history.

(56) References Cited

U.S. PATENT DOCUMENTS

| | | |
|---|---|---|
| 4,931,439 A | 6/1990 | Kristinsson |
| 2013/0102468 A1 | 4/2013 | Shibayama |
| 2014/0106968 A1 | 4/2014 | Taggi |

FOREIGN PATENT DOCUMENTS

CN    107266378 A    10/2017

*Primary Examiner* — Erin E Hirt
(74) *Attorney, Agent, or Firm* — Volpe Koenig

(57) ABSTRACT

The present invention belongs to the technical field of pesticides, particularly relates to sulfonyl-structure-containing triazinone derivatives, their preparation methods, and their uses in insect killing and/or bacterium killing. The sulfonyl-structure-containing triazinone derivatives are compounds represented by formula ($I_a$) or ($I_b$). The sulfonyl-structure-containing triazinone derivatives provided in the present invention exhibit outstanding insecticidal activity as well as bactericidal activity.

9 Claims, No Drawings

SULFONYL-STRUCTURE-CONTAINING TRIAZINONE DERIVATIVES, THEIR PREPARATION METHODS AND THEIR USES IN INSECT KILLING AND/OR BACTERIUM KILLING

CROSS REFERENCE TO RELATED APPLICATIONS

This application is a 35 USC § 371 national stage application of PCT/CN2017/102600, which was filed Sep. 21, 2017 and is incorporated herein by reference as if fully set forth.

FIELD OF THE INVENTION

The present invention belongs to the technical field of pesticides, particularly relates to sulfonyl-structure-containing triazinone derivatives, their preparation methods, and their uses in insect killing and/or fungus killing.

BACKGROUND OF THE INVENTION

Pymetrozine is a new heterocyclic insecticide discovered by Ciba-Geigy in 1988, whose characteristics including unique action, high selectivity, free of cross-resistance compared with conventional insecticides, and environmental safety, etc., and can attain a unique prevention and control effect against pests with piercing-sucking mouthpart, especially against aphides. Therefore, since pymetrozine emerged, it has been widely applied in prevention and control of aphides, whiteflies, and black-tailed leafhoppers for field crops and ornamental plants. However, owing to the unique action of pymetrozine, there are only three commercial insecticide products in this category up to now, i.e., pymetrozine, R-768 and pyrifluquinazon. Summarized on the basis of literatures, it is found that the researches on these insecticides mainly focus on triazinone ring and pyridine ring; however, there is no report on utilization of sulfone or sulfoxide as common active groups in the molecular designs of medicines and pesticides. As more and more attentions are paid to environmental protection all over the world, it is an urgent task to develop efficient, low-toxic, and environmentally friendly insecticides in the pymetrozine category in present agricultural production.

SUMMARY OF THE INVENTION

The object of the present invention is to provide sulfonyl-structure-containing triazinone derivatives, their preparation methods, and their uses in insect killing and/or fungus killing. The sulfonyl-structure-containing triazinone derivatives in this patent application exhibit outstanding insecticidal activity as well as fungicidal activity.

In a first aspect, the present invention provides a sulfonyl-structure-containing triazinone derivative, which is a compound represented by formula (Ia):

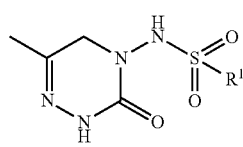

formula (I$_a$)

wherein R$^1$ is C1-C12 alkyl, C3-C6 cycloalkyl, substituted or unsubstituted phenyl, substituted or unsubstituted naphthyl, substituted or unsubstituted benzyl, substituted or unsubstituted phenethyl, substituted or unsubstituted phenylpropyl, substituted or unsubstituted phenylbutyl, nitrogen-containing heterocycle containing 1-10 carbon atoms, oxygen-containing heterocycle containing 1-10 carbon atoms, or sulfur-containing heterocycle containing 1-10 carbon atoms; the substituents of the substituted phenyl, the substituted naphthyl, the substituted benzyl, the substituted phenethyl, the substituted phenylpropyl, and the substituted phenylbutyl are one or more substituents respectively and independently selected from the group consisting of hydroxyl, halogen, cyano, nitro, ester group, trifluoromethyl, trifluoromethoxy, amido, C1-C6 alkyl, C1-C6 alkoxy, carbonyloxy substituted by C1-C4 alkyl, or carbonyloxy substituted by C1-C4 alkoxy.

In a second aspect, the present invention provides a preparation method of the above-mentioned triazinone derivative, which comprises: controlling amino-triazinone represented by formula (II) and sulfonyl chloride compound represented by formula (III) to have a substitution reaction in an organic solvent in the presence of an acid binding agent to obtain a compound represented by formula (I$_a$);

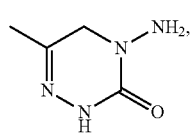

formula (II)

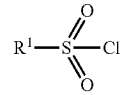

formula (III)

In a third aspect, the present invention provides a sulfonyl-structure-containing triazinone derivative, which is a compound represented by formula (I$_b$):

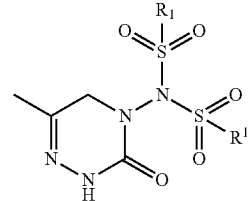

formula (I$_b$)

wherein each R$^1$ is respectively and independently selected from the group consisting of C1-C12 alkyl, C3-C6 cycloalkyl, substituted or unsubstituted phenyl, substituted or unsubstituted naphthyl, substituted or unsubstituted benzyl, substituted or unsubstituted phenethyl, substituted or unsubstituted phenylpropyl, substituted or unsubstituted phenylbutyl, nitrogen-containing heterocycle containing 1-10 carbon atoms, oxygen-containing heterocycle containing 1-10 carbon atoms, and sulfur-containing heterocycle containing 1-10 carbon atoms; the substituents of the substituted phenyl, the substituted naphthyl, the substituted benzyl, the substituted phenethyl, the substituted phenylpropyl, and the substituted phenylbutyl are one or more substituents respectively and independently selected from the group consisting of hydroxyl, halogen, cyano, nitro, ester group, trifluoromethyl, trifluoromethoxy, amido, C1-C6 alkyl, C1-C6 alkoxy, carbonyloxy substituted by C1-C4 alkyl, and carbonyloxy substituted by C1-C4 alkoxy. In a fourth aspect, the present invention provides a preparation method of the above-mentioned triazinone derivative, which comprises: controlling amino-triazinone represented by formula (II) and sulfonyl chloride compound represented by formula (III) to have a substitution reaction in an organic solvent in the presence of an acid binding agent to obtain a compound represented by formula ($I_b$);

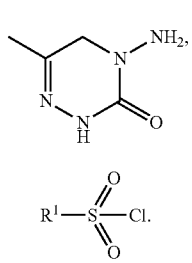

formula (II)

formula (III)

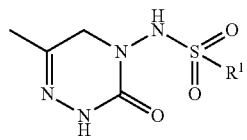

In a fifth aspect, the present invention provides a use of the above-mentioned triazinone derivative in insect killing.

In a sixth aspect, the present invention provides a use of the above-mentioned triazinone derivative in fungus killing.

The triazinone derivatives provided in the present invention exhibit outstanding insecticidal activity as well as fungicidal activity.

DETAILED DESCRIPTION OF THE EXAMPLES

The end points and any value in the ranges disclosed in the present invention are not limited to the exact ranges or values; instead, those ranges or values shall be comprehended as encompassing values that are close to those ranges or values. For numeric ranges, the end points of the ranges, the end points of the ranges and the discrete point values, and the discrete point values may be combined to obtain one or more new numeric ranges, which shall be deemed as having been disclosed specifically in this document.

In a first aspect, the present invention provides a sulfonyl-structure-containing triazinone derivative, which is a compound represented by formula ($I_a$):

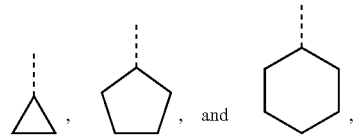

formula ($I_a$)

wherein $R^1$ is C1-C12 alkyl, C3-C6 cycloalkyl, substituted or unsubstituted phenyl, substituted or unsubstituted naphthyl, substituted or unsubstituted benzyl, substituted or unsubstituted phenethyl, substituted or unsubstituted phenylpropyl, substituted or unsubstituted phenylbutyl, nitrogen-containing heterocycle containing 1-10 carbon atoms, oxygen-containing heterocycle containing 1-10 carbon atoms, or sulfur-containing heterocycle containing 1-10 carbon atoms; the substituents of the substituted phenyl, the substituted naphthyl, the substituted benzyl, the substituted phenethyl, the substituted phenylpropyl, and the substituted phenylbutyl are one or more substituents respectively and independently selected from the group consisting of hydroxyl, halogen, cyano, nitro, ester, trifluoromethyl, trifluoromethoxy, amido, C1-C6 alkyl, C1-C6 alkoxy, carbonyloxy substituted by C1-C4 alkyl, and carbonyloxy substituted by C1-C4 alkoxyl.

According to the present invention, the sulfonyl-structure-containing triazinone derivatives provided in the first aspect and third aspect of the present invention may be generally represented by the following formula (I):

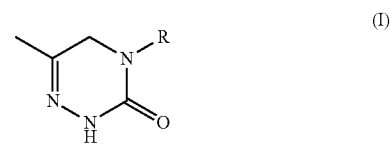

(I)

In the present invention, examples of the C1-C12 alkyl may include methyl, ethyl, n-propyl, isopropyl, n-butyl, isobutyl, sec-butyl, tert-butyl, n-pentyl, n-hexyl, n-heptyl, n-octyl, n-nonyl, n-decyl, n-hendecyl, and n-dodecyl, etc.

The C1-C6 alkyl and the C1-C4 alkyl may be selected from the above-mentioned examples of alkyls, as long as they meet the corresponding criteria.

The C1-C6 alkoxy may be an alkoxy formed by an example of alkyl that meets the criterion of 1-6 carbon atoms.

The examples of the C3-C6 cycloalkyl may be etc., for example.

The nitrogen-containing heterocycle containing 1-10 carbon atoms may be an unsaturated nitrogen-containing heterocycle or a saturated nitrogen-containing heterocycle, as long as the ring structure of the heterocycle employs nitrogen as a structural atom and the heterocycle has 1-10 carbon atoms. For example, the nitrogen-containing heterocycle containing 1-10 carbon atoms may be selected from the group consisting of unsubstituted pyrrole or pyrrole substituted by C1-C6 alkyl, unsubstituted pyrroline or pyrroline substituted by C1-C6 alkyl, unsubstituted imidazole or imidazole substituted by C1-C7 alkyl, unsubstituted imidazoline or imidazoline substituted by C1-C7 alkyl, unsubstituted pyridine or pyridine substituted by C1-C5 alkyl, unsubstituted pyridinoline or pyridinoline substituted by C1-C5 alkyl, unsubstituted parazole or parazole substituted by C1-C7 alkyl, unsubstituted pyrazolinone or pyrazolinone substituted by C1-C7 alkyl, unsubstituted thiazole or thiazole substituted by C1-C7 alkyl, unsubstituted thiazoline or thiazoline substituted by C1-C7 alkyl, unsubstituted oxazole or oxazole substituted by C1-C7 alkyl, and unsubstituted oxazoline or oxazoline substituted by C1-C7 alkyl, etc. Wherein the alkyl that serves as a substituent may be selected appropriately from the examples of alkyls described above, and the alkyl substitution may be a single-site substitution or a multi-site substitution. There is no particular restriction on the substitution in the present invention.

The oxygen-containing heterocycle containing 1-10 carbon atoms may be an unsaturated oxygen-containing heterocycle or a saturated oxygen-containing heterocycle, as long as the ring structure of the heterocycle employs oxygen as a structural atom and the heterocycle has 1-10 carbon atoms. For example, the oxygen-containing heterocycle containing 1-10 carbon atoms may be selected from the group consisting of unsubstituted furan or furan substituted by C1-C6 alkyl, unsubstituted tetrahedrafuran or tetrahedrafuran substituted by C1-C6 alkyl, unsubstituted oxazole or oxazole substituted by C1-C7 alkyl, unsubstituted oxazoline or oxazoline substituted by C1-C7 alkyl, unsubstituted 1,3-benzodioxole or 1,3-benzodioxole substituted by C1-C3 alkyl, and unsubstituted 1,4-benzodioxine or 1,4-benzodioxine substituted by C1-C2 alkyl, etc.

The sulfur-containing heterocycle containing 1-10 carbon atoms may be an unsaturated sulfur-containing heterocycle or a saturated sulfur-containing heterocycle, as long as the ring structure of the heterocycle employs sulfur as a structural atom and the heterocycle has 1-10 carbon atoms. For example, the sulfur-containing heterocycle containing 1-10 carbon atoms may be selected from the group consisting of unsubstituted thiophene or thiophene substituted by C1-C6 alkyl, unsubstituted tetrahedrathiophene or tetrahedrathiophene substituted by C1-C6 alkyl, unsubstituted thiazole or thiazole substituted by C1-C7 alkyl, and unsubstituted thiazoline or thiazoline substituted by C1-C7 alkyl, etc.

Preferably, $R^1$ is C1-C8 alkyl, C3-C6 cycloalkyl, substituted or unsubstituted phenyl, substituted or unsubstituted naphthyl, substituted or unsubstituted benzyl, substituted or unsubstituted phenethyl, substituted or unsubstituted phenylpropyl, substituted or unsubstituted phenylbutyl, nitrogen-containing heterocycle containing 2-8 carbon atoms, oxygen-containing heterocycle containing 2-8 carbon atoms, or sulfur-containing heterocycle containing 2-8 carbon atoms; the substituents of the substituted phenyl, the substituted naphthyl, the substituted benzyl, the substituted phenethyl, the substituted phenylpropyl, and the substituted phenylbutyl are one or more substituents respectively and independently selected from the group consisting of hydroxyl, F, Cl, Br, I, cyano, nitro, —COOCH₃, —COOCH₂CH₃, trifluoromethyl, trifluoromethoxy, —NH—CO—CH₃, —NH—CO—CH₂CH₃, methyl, ethyl, n-propyl, isopropyl, n-butyl, isobutyl, sec-butyl, tert-butyl, n-pentyl, methoxy, ethoxy, n-propoxy, isopropoxy, n-butoxy, isobutoxy, sec-butoxy, tert-butoxy, n-pentyloxy, C1-C5 alkyl, C1-C5 alkoxy, —O—CO—CH₃, —O—CO—CH₂CH₃, —O—CO—O—CH₃, and —O—CO—O—CH₂CH₃.

In a preferred embodiment of the present invention, the compound represented by formula ($I_a$) is at least one of the compounds represented by the following formulae:

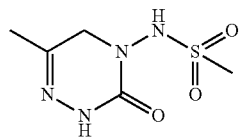

$I_a$-1

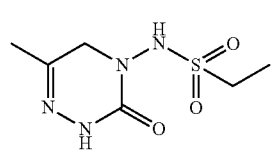

$I_a$-2

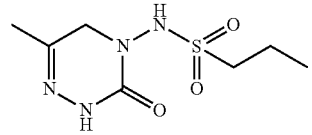

$I_a$-3

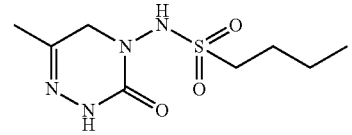

$I_a$-4

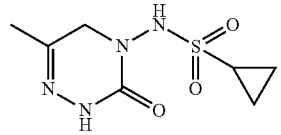

$I_a$-5

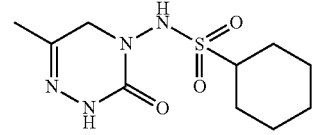

$I_a$-6

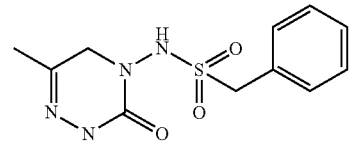

$I_a$-7

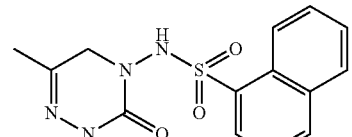

$I_a$-8

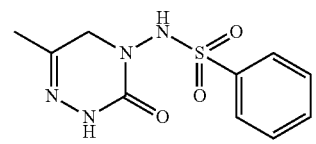

$I_a$-9

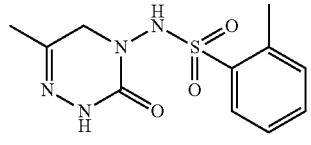

$I_a$-10

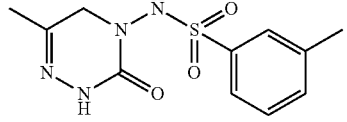

$I_a$-11

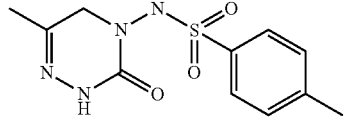

$I_a$-12

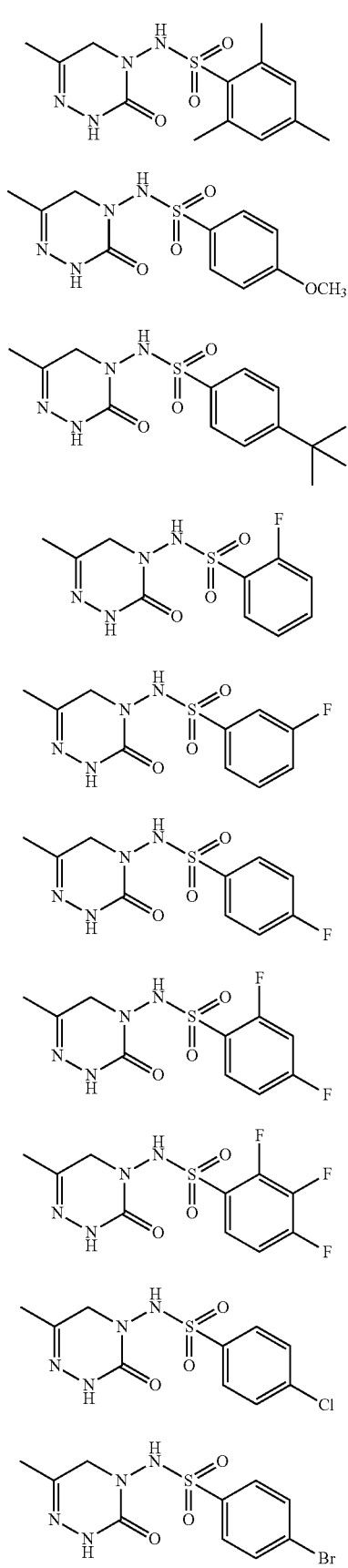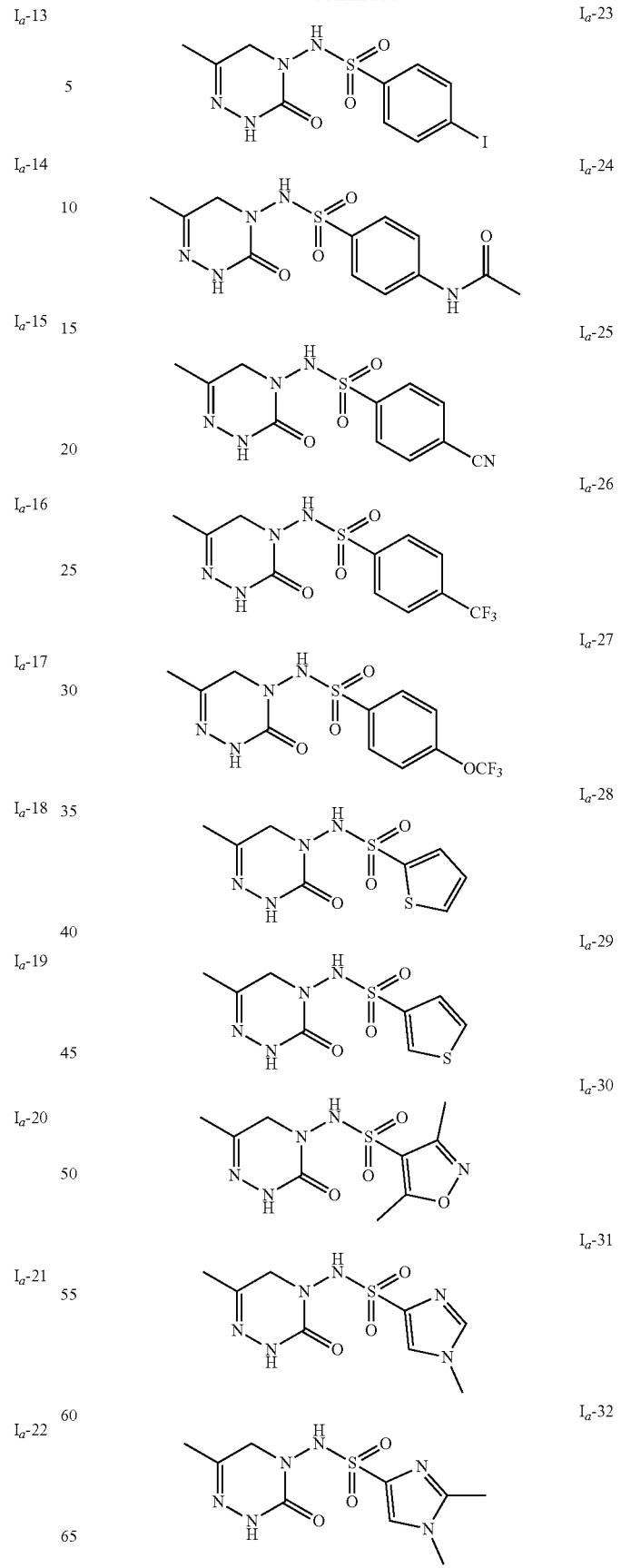

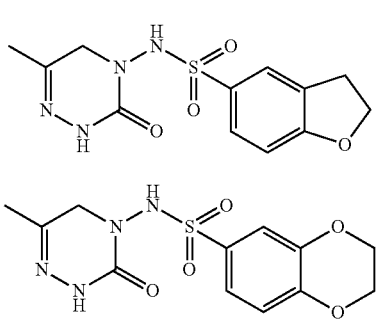

In a second aspect, the present invention provides a preparation method of the above-mentioned triazinone derivative, which comprises: controlling amino-triazinone represented by formula (II) and sulfonyl chloride compound represented by formula (III) to have a substitution reaction in an organic solvent in the presence of an acid binding agent to obtain a compound represented by formula ($I_a$);

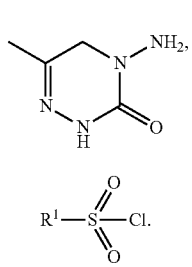

The preparation procedure may be expressed by the following route I:
route I:

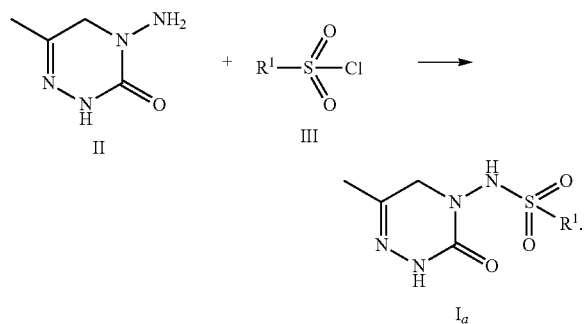

According to the present invention, the compound represented by formula (III) may be selected specifically according to the required formula ($I_a$), and the $R^1$ in the formula has been described above and will not be further detailed.

Preferably, the molar ratio of the amino-triazinone represented by formula (II) to the sulfonyl chloride compound represented by formula (III) is 1:0.8-1.2, preferably is 1:1-1.1.

Preferably, the acid binding agent is at least one of the agents selected from the group consisting of sodium carbonate, potassium carbonate, cesium carbonate, triethylamine, and pyridine.

The dosage of the acid binding agent may vary within a wide range. For example, the molar ratio of the amino-triazinone represented by formula (II) to the acid binding agent may be 1:0.08-0.5, preferably is 1:0.1-0.3. The pyridine may also be used as the solvent in the above-mentioned method. To that end, when pyridine is used as a solvent, the dose of pyridine is not limited to the dose specified above, as long as the requirement for the dose of the solvent is met.

Preferably, the organic solvent is at least one of the solvents selected from the group consisting of methanol, ethanol, pyridine, N,N-dimethyl formamide and dimethyl sulfoxide.

Preferably, the organic solvent is dosed so that the concentration of the amino-triazinone represented by formula (II) is 0.05-0.5 mmol/mL.

Preferably, the conditions of the substitution reaction include: temperature: 15-40° C. (preferably 20-35° C.); time: 4-12 h.

In a third aspect, the present invention provides a sulfonyl-structure-containing triazinone derivative, which is a compound represented by formula ($I_b$):

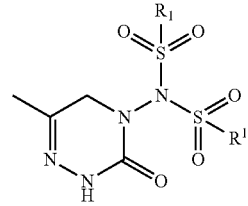

wherein each $R^1$ is respectively and independently selected from the group consisting of C1-C12 alkyl, C3-C6 cycloalkyl, substituted or unsubstituted phenyl, substituted or unsubstituted naphthyl, substituted or unsubstituted benzyl, substituted or unsubstituted phenethyl, substituted or unsubstituted phenylpropyl, substituted or unsubstituted phenylbutyl, nitrogen-containing heterocycle containing 1-10 carbon atoms, oxygen-containing heterocycle containing 1-10 carbon atoms, or sulfur-containing heterocycle containing 1-10 carbon atoms; the substituents of the substituted phenyl, the substituted naphthyl, the substituted benzyl, the substituted phenethyl, the substituted phenylpropyl, and the substituted phenylbutyl are one or more substituents respectively and independently selected from the group consisting of hydroxyl, halogen, cyano, nitro, ester, trifluoromethyl, trifluoromethoxy, amido, C1-C6 alkyl, C1-C6 alkoxy, carbonyloxy substituted by C1-C4 alkyl, and carbonyloxy substituted by C1-C4 alkoxy.

In an embodiment of the present invention, the $R^1$ in the present invention may be selected from the group consisting of C1-C12 alkyl, C3-C6 cycloalkyl, phenyl, benzyl, phenethyl, phenylpropyl, phenylbutyl, C1-C10 nitrogen-containing heterocycle, C1-C10 oxygen-containing heterocycle, C1-C10 sulfur-containing heterocycle, or substituted phenyl (wherein the substituent may be hydrogen, hydroxyl, halogen, cyano, nitro, ester, fluorine, trifluoromethyl, trifluoromethoxy, amido, C1-C5 alkyl, C1-C6 alkoxy, C1-C4 alkyl carbonyloxy, or C1-C4 alkoxy carbonyloxy; and may contain 2-3 substituents described above at the same time).

Wherein the two $R^1$ in the formula ($I_b$) may be the same or different, and may be selected respectively and independently; wherein the $R^1$ in the formula ($I_b$) may be selected from relevant groups in the formula ($I_a$) described above, and there is no further restriction on it in the present invention.

Preferably, each $R^1$ is respectively and independently selected from the group consisting of C1-C8 alkyl, C3-C6 cycloalkyl, substituted or unsubstituted phenyl, substituted or unsubstituted naphthyl, substituted or unsubstituted benzyl, substituted or unsubstituted phenethyl, substituted or unsubstituted phenylpropyl, substituted or unsubstituted phenylbutyl, nitrogen-containing heterocycle containing 2-8 carbon atoms, oxygen-containing heterocycle containing 2-8 carbon atoms, and sulfur-containing heterocycle containing 2-8 carbon atoms; the substituents of the substituted phenyl, the substituted naphthyl, the substituted benzyl, the substituted phenethyl, the substituted phenylpropyl, and the substituted phenylbutyl are one or more substituents respectively and independently selected from the group consisting of hydroxyl, F, Cl, Br, I, cyano, nitro, —COOCH₃, —COOCH₂CH₃, trifluoromethyl, trifluoromethoxy, —NH—CO—CH₃, —NH—CO—CH₂CH₃, methyl, ethyl, n-propyl, isopropyl, n-butyl, isobutyl, sec-butyl, tert-butyl, n-pentyl, methoxy, ethoxy, n-propoxy, isopropoxy, n-butoxy, isobutoxy, sec-butoxy, tert-butoxy, n-pentyloxy, C1-C5 alkyl, C1-C5 alkoxy, —O—CO—CH₃, —O—CO—CH₂CH₃, —O—CO—O—CH₃, and —O—CO—O—CH₂CH₃.

In a preferred embodiment of the present invention, the compound represented by formula ($I_b$) is at least one of the compounds represented by the following formulae:

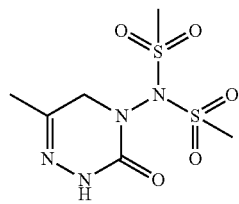

$I_b$-1

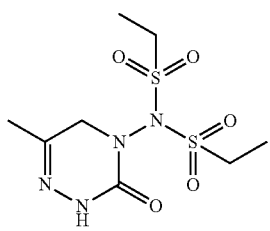

$I_b$-2

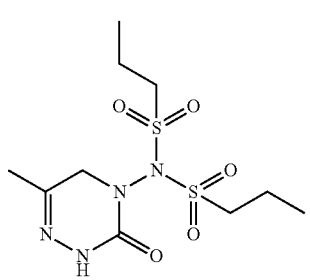

$I_b$-3

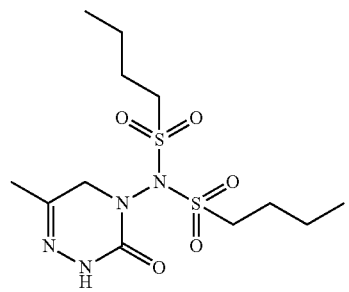

$I_b$-4

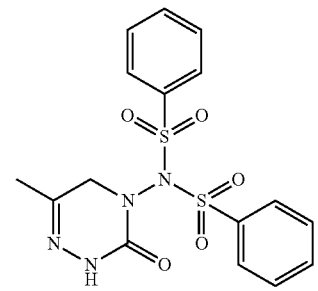

$I_b$-5

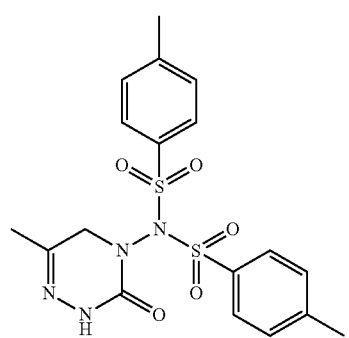

$I_b$-6

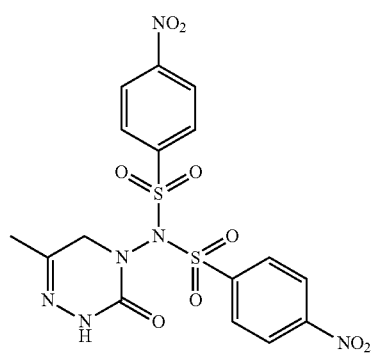

$I_b$-7

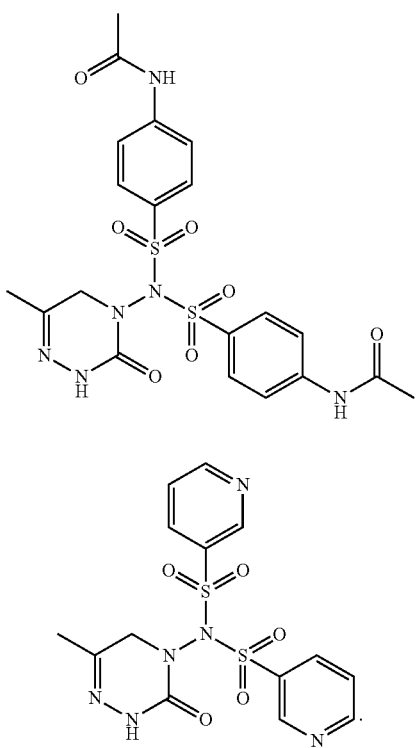

I_b-8

I_b-9

In a fourth aspect, the present invention provides a preparation method of the above-mentioned triazinone derivative, which comprises: controlling amino-triazinone represented by formula (II) and sulfonyl chloride compound represented by formula (III) to have a substitution reaction in an organic solvent in the presence of an acid binding agent to obtain a compound represented by formula (I_b);

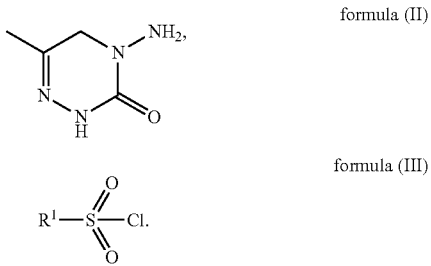

formula (II)

formula (III)

The method may be generally summarized as the following route: triazinone (II) reacts with different sulfonyl chlorides to obtain the compound I_b;

route II:

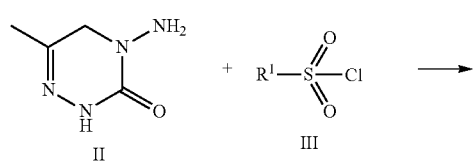

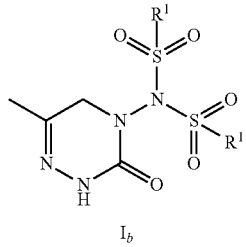

I_b wherein the compound represented by formula (III) may be specifically selected according to the required formula (I_b), and the R$^1$ in the formula has been described above, and will not be further detailed here.

Preferably, the molar ratio of the amino-triazinone represented by formula (II) to the sulfonyl chloride compound represented by formula (III) is 1:1.8-2.5, preferably is 1:2-2.4.

Preferably, the acid binding agent is at least one of the agents selected from the group consisting of sodium carbonate, potassium carbonate, cesium carbonate, triethylamine, and pyridine.

The dosage of the acid binding agent may vary within a wide range. For example, the molar ratio of the amino-triazinone represented by formula (II) to the acid binding agent may be 1:0.08-0.5, preferably is 1:0.1-0.3. The pyridine may also be used as the solvent in the above-mentioned method. To that end, when pyridine is used as a solvent, the dose of pyridine is not limited to the dose specified above, as long as the requirement for the dose of the solvent is met.

Preferably, the organic solvent is at least one of the solvents selected from the group consisting of methanol, ethanol, pyridine, N,N-dimethyl formamide and dimethyl sulfoxide.

Preferably, the organic solvent is dosed so that the concentration of the amino-triazinone represented by formula (II) is 0.05-0.5 mmol/mL.

Preferably, the conditions of the substitution reaction include: temperature: 15-40° C. (preferably 20-35° C.); time: 4-12 h.

In a fifth aspect, the present invention provides a use of the above-mentioned triazinone derivative in insect killing.

The triazinone derivatives provided in the present invention have relatively high insecticidal activity, and have relatively high insecticidal activity especially against aphides, mosquito larvae, cotton bollworms, maize borers, and armyworms.

For the purpose of obtaining relatively high insecticidal activity, preferably, the sulfonyl-structure-containing triazinone derivative in the present invention is at least one of the following compounds:
2-methyl-N-(6-methyl-3-oxo-2,3-dihydro-1,2,4-triazin-4 (5H)-yl)benzenesulfonamide (Ia-10);
3-methyl-N-(6-methyl-3-oxo-2,3-dihydro-1,2,4-triazin-4 (5H)-yl)benzenesulfonamide (Ia-11);
4-methyl-N-(6-methyl-3-oxo-2,3-dihydro-1,2,4-triazin-4 (5H)-yl)benzenesulfonamide (Ia-12);
2,4,6-trimethyl-N-(6-methyl-3-oxo-2,3-dihydro-1,2,4-triazin-4(5H)-yl)benzenesulfonamide (Ia-13);
4-methoxy-N-(6-methyl-3-oxo-2,3-dihydro-1,2,4-triazin-4 (5H)-yl)benzenesulfonamide (Ia-14);
4-tert-butyl-N-(6-methyl-3-oxo-2,3-dihydro-1,2,4-triazin-4 (5H)-yl)benzenesulfonamide (Ia-15);
4-bromo-N-(6-methyl-3-oxo-2,3-dihydro-1,2,4-triazin-4 (5H)-yl)benzenesulfonamide (Ia-22).

Particularly, the sulfonyl-structure-containing triazinone derivatives in the present invention exhibit outstanding insecticidal activity against aphids, wherein the compounds $I_a$-10, $I_a$-11, $I_a$-12, $I_a$-13, $I_a$-14 and $I_a$-15 exhibit insecticidal activity with mortalities of 25%, 15%, 30%, 10%, 35%, and 10% respectively at a concentration of 2.5 mg/kg, while pymetrozine has no insecticidal activity at the same concentration. Besides, some of the compounds exhibit satisfactory insecticidal activity against mosquito larvae, wherein at a concentration of 1 mg/kg, the compounds $I_a$-19, $I_a$-23 and $I_a$-26 exhibit insecticidal activity with mortalities of 60%, 30% and 20% against mosquito larvae; especially, the compound $I_a$-22 exhibits insecticidal activity with a mortality of 40% against mosquito larvae at a concentration of 0.5 mg/kg. In addition, all of the compounds exhibit insecticidal activity against cotton bollworms, maize borers, and armyworms.

The present invention further provides an insecticidal method that utilizes the above-mentioned triazinone derivative as an insecticide.

In a sixth aspect, the present invention provides a use of the above-mentioned triazinone derivative in fungus killing.

The triazinone derivatives provided in the present invention have high insecticidal activity, especially against at least one of the pathogenic fungi that may cause tomato early blight, wheat head blight, potato late blight, *Capsicum phytophthora* blight, *Sclerotinia* rot of colza, cucumber gray mold, rice sheath blight, cucumber *Fusarium* wilt, *Cercospora* brown spot of peanut, apple ring rot, wheat sheath blight, corn southern leaf blight, watermelon anthracnose, and rice bakanae disease.

For the purpose of obtaining higher fungicidal activity, preferably, the sulfonyl-structure-containing triazinone derivative in the present invention is at least one of the following compounds:

2-methyl-N-(6-methyl-3-oxo-2,3-dihydro-1,2,4-triazin-4 (5H)-yl)benzenesulfonamide ($I_a$-10);

3-methyl-N-(6-methyl-3-oxo-2,3-dihydro-1,2,4-triazin-4 (5H)-yl)benzenesulfonamide ($I_a$-11);

4-methyl-N-(6-methyl-3-oxo-2,3-dihydro-1,2,4-triazin-4 (5H)-yl)benzenesulfonamide ($I_a$-12);

2,4,6-trimethyl-N-(6-methyl-3-oxo-2,3-dihydro-1,2,4-triazin-4(5H)-yl)benzenesulfonamide ($I_a$-13);

4-methoxy-N-(6-methyl-3-oxo-2,3-dihydro-1,2,4-triazin-4 (5H)-yl)benzenesulfonamide ($I_a$-14);

4-tert-butyl-N-(6-methyl-3-oxo-2,3-dihydro-1,2,4-triazin-4 (5H)-yl)benzenesulfonamide ($I_a$-15);

4-bromo-N-(6-methyl-3-oxo-2,3-dihydro-1,2,4-triazin-4 (5H)-yl)benzenesulfonamide ($I_a$-22).

Wherein especially the compounds $I_a$-4, $I_a$-12 and $I_b$-5 exhibit outstanding fungicidal activity against a variety of pathogenic fungi at a concentration of 50 mg/kg.

The present invention further provides a fungicidal method that utilizes the above-mentioned triazinone derivative as a fungicide.

The following examples and biological test results can be used to further illustrate the present invention, but not mean to constitute any limitation to the present invention.

Example 1

(1) Synthesis of N-(6-methyl-3-oxo-2,3-dihydro-1, 2,4-triazin-4(5H)-yl)-methylsulfonylamide ($I_a$-1)

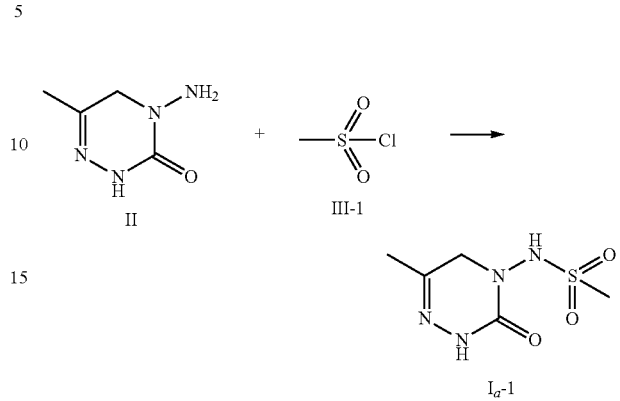

Amino-triazinone (0.26 g, 2 mmol, from TCI (Shanghai) Development Co., Ltd.) and pyridine (20 mL) are added into a 100 mL single-neck flask and stirred to dissolve, then methylsulfonyl chloride (0.24 g, 2.1 mmol, from Energy Chemical Co., Ltd.) is added into the flask, and the mixture is stirred and held overnight at room temperature, the reaction is monitored with a TLC till it is finished. After desolvation of the reaction liquid under reduced pressure, water is added to the mixture and the product is extracted with methylene chloride and then washed twice with saturated sodium chloride solution and dried with sodium sulfate; next, the product is treated by chromatography in a silica-gel column with methylene chloride/methanol (150: 1-100:1); thus, 0.32 g white solid is obtained, the yield is 78%, and the melting point of the white solid is 191-192° C. $^1$H NMR (300 MHz, DMSO-$d_6$) δ 10.00 (s, 1H, NH), 9.83 (s, 1H, NH), 4.15 (s, 2H, CH$_2$), 3.01 (s, 3H, CH$_3$), 1.86 (s, 3H, CH$_3$); $^{13}$C NMR (100 MHz, DMSO-$d_6$) δ 151.4, 146.0, 53.9, 41.1, 20.1. ESI-HRMS (m/z): Calcd. for $C_5H_{11}N_4O_3S$ [M+H]$^+$ 207.0546; found 207.0548.

(2) Synthesis of Compounds $I_a$-2~$I_a$-34 by Repeating the Steps for $I_a$-1

Except:
In the preparation of the compound $I_a$-2, the methylsulfonyl chloride is replaced with ethylsulfonyl chloride (from Energy Chemical Co., Ltd.) in the same molar mass;

In the preparation of the compound $I_a$-3, the methylsulfonyl chloride is replaced with n-propylsulfonyl chloride (from Beijing Innochem Science & Technology Co., Ltd.) in the same molar mass;

In the preparation of the compound $I_a$-4, the methylsulfonyl chloride is replaced with n-butylsulfonyl chloride (from Beijing Innochem Science & Technology Co., Ltd.) in the same molar mass;

In the preparation of the compound $I_a$-5, the methylsulfonyl chloride is replaced with

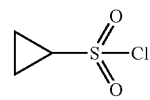

(from Beijing Innochem Science & Technology Co., Ltd.) in the same molar mass;

In the preparation of the compound $I_a$-6, the methylsulfonyl chloride is replaced with

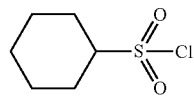

(from Beijing Innochem Science & Technology Co., Ltd.) in the same molar mass;

In the preparation of the compound $I_a$-7, the methylsulfonyl chloride is replaced with

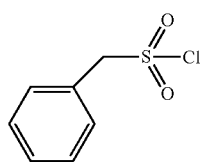 [SMILES: O=S(=O)(Cl)Cc1ccccc1]

(from Tianjin Heowns Biochemical Technology Co., Ltd.) in the same molar mass;

In the preparation of the compound $I_a$-8, the methylsulfonyl chloride is replaced with

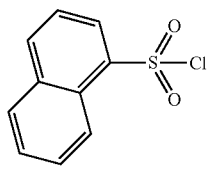

(from J&K Scientific Ltd.) in the same molar mass;

In the preparation of the compound $I_a$-9, the methylsulfonyl chloride is replaced with

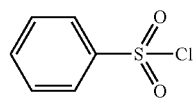

(from Tianjin Reagents Co., Ltd.) in the same molar mass;

In the preparation of the compound $I_a$-10, the methylsulfonyl chloride is replaced with

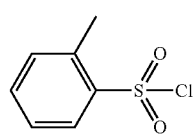

(from Energy Chemical Co., Ltd.) in the same molar mass;

In the preparation of the compound $I_a$-11, the methylsulfonyl chloride is replaced with

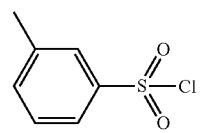

(from Shanghai Boka Chemical Technology Co., Ltd.) in the same molar mass;

In the preparation of the compound $I_a$-12, the methylsulfonyl chloride is replaced with

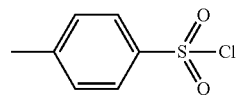

(from Shanghai Aladdin Bio-Chem Technology Co., LTD) in the same molar mass;

In the preparation of the compound $I_a$-13, the methylsulfonyl chloride is replaced with

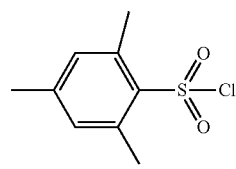

(from Energy Chemical Co., Ltd.) in the same molar mass;

In the preparation of the compound $I_a$-14, the methylsulfonyl chloride is replaced with

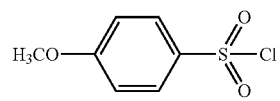 [SMILES: COc1ccc(S(=O)(=O)Cl)cc1]

(from Shanghai Aladdin Bio-Chem Technology Co., LTD) in the same molar mass;

In the preparation of the compound $I_a$-15, the methylsulfonyl chloride is replaced with

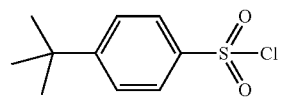

(from Energy Chemical Co., Ltd.) in the same molar mass;

In the preparation of the compound $I_a$-16, the methylsulfonyl chloride is replaced with

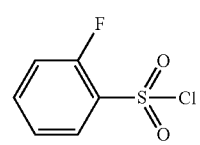 [SMILES: O=S(=O)(Cl)c1ccccc1F]

(from Shanghai Boka Chemical Technology Co., Ltd.) in the same molar mass;

In the preparation of the compound $I_a$-17, the methylsulfonyl chloride is replaced with

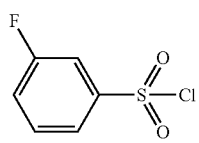

(from Shanghai Boka Chemical Technology Co., Ltd.) in the same molar mass;
In the preparation of the compound $I_a$-18, the methylsulfonyl chloride is replaced with

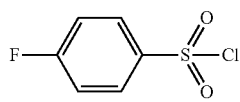

(from Shanghai Boka Chemical Technology Co., Ltd.) in the same molar mass;
In the preparation of the compound $I_a$-19, the methylsulfonyl chloride is replaced with

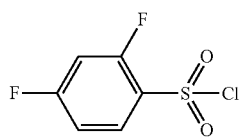 [SMILES: O=S(=O)(Cl)c1ccc(F)cc1F]

(from Shanghai Boka Chemical Technology Co., Ltd.) in the same molar mass;
In the preparation of the compound $I_a$-20, the methylsulfonyl chloride is replaced with

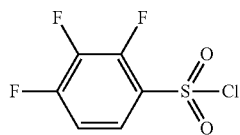 [SMILES: O=S(=O)(Cl)c1ccc(F)c(F)c1F]

(from Beijing Innochem Science & Technology Co., Ltd.) in the same molar mass;
In the preparation of the compound $I_a$-21, the methylsulfonyl chloride is replaced with

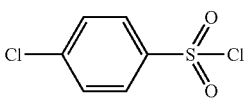 [SMILES: O=S(=O)(Cl)c1ccc(Cl)cc1]

(from Tianjin Heowns Biochemical Technology Co., Ltd.) in the same molar mass;
In the preparation of the compound $I_a$-22, the methylsulfonyl chloride is replaced with

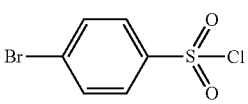

(from Tianjin Heowns Biochemical Technology Co., Ltd.) in the same molar mass;

In the preparation of the compound $I_a$-23, the methylsulfonyl chloride is replaced with

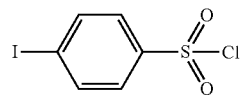

(from Shanghai Boka Chemical Technology Co., Ltd.) in the same molar mass;
In the preparation of the compound $I_a$-24, the methylsulfonyl chloride is replaced with

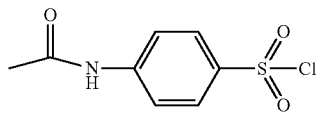

(from Shanghai Boka Chemical Technology Co., Ltd.) in the same molar mass;
In the preparation of the compound $I_a$-25, the methylsulfonyl chloride is replaced with

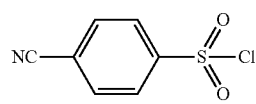

(from Shanghai Boka Chemical Technology Co., Ltd.) in the same molar mass;
In the preparation of the compound $I_a$-26, the methylsulfonyl chloride is replaced with

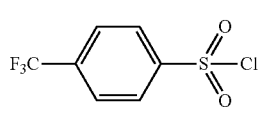

(from Shanghai Boka Chemical Technology Co., Ltd.) in the same molar mass;
In the preparation of the compound $I_a$-27, the methylsulfonyl chloride is replaced with

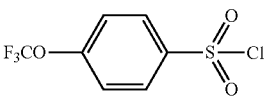

(from Shanghai Boka Chemical Technology Co., Ltd.) in the same molar mass;
In the preparation of the compound $I_a$-28, the methylsulfonyl chloride is replaced with

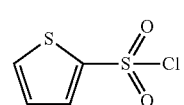
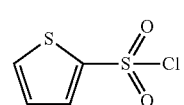
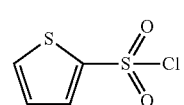

(from Energy Chemical Co., Ltd.) in the same molar mass;
In the preparation of the compound $I_a$-29, the methylsulfonyl chloride is replaced with

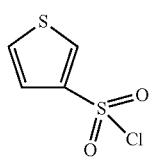

(from Energy Chemical Co., Ltd.) in the same molar mass;
In the preparation of the compound I$_a$-30, the methylsulfonyl chloride is replaced with

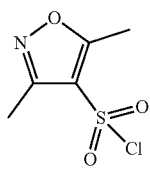

(from Energy Chemical Co., Ltd.) in the same molar mass;
In the preparation of the compound I$_a$-31, the methylsulfonyl chloride is replaced with

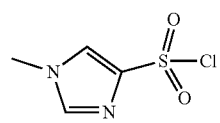

(from Energy Chemical Co., Ltd.) in the same molar mass;
In the preparation of the compound I$_a$-32, the methylsulfonyl chloride is replaced with

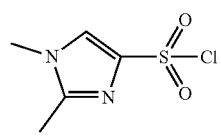

(from Energy Chemical Co., Ltd.) in the same molar mass;
In the preparation of the compound I$_a$-33, the methylsulfonyl chloride is replaced with

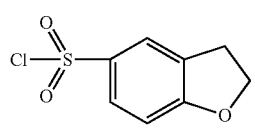 [SMILES: O=S(=O)(Cl)c1ccc2c(c1)CCO2]

(from Beijing Innochem Science & Technology Co., Ltd.) in the same molar mass;
In the preparation of the compound I$_a$-34, the methylsulfonyl chloride is replaced with

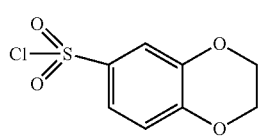 [SMILES: O=S(=O)(Cl)c1ccc2c(c1)OCCO2]

(from Beijing Innochem Science & Technology Co., Ltd.) in the same molar mass;

The obtained compounds are characterized as follows:

N-(6-methyl-3-oxo-2,3-dihydro-1,2,4-triazin-4(5H)-yl)-ethylsulfonamide (I$_a$-2)

White solid, yield 76%, melting point 206-208° C. $^1$H NMR (300 MHz, DMSO-d$_6$) δ 9.98 (s, 1H, NH), 9.79 (s, 1H, NH), 4.15 (s, 2H, CH$_2$), 3.10 (q, J=7.2 Hz, 2H, CH$_2$CH$_3$), 1.85 (s, 3H, CH$_3$), 1.27 (t, J=7.2 Hz, 3H, CH$_2$CH$_3$); $^{13}$C NMR (100 MHz, DMSO-d$_6$) δ 151.2, 145.7, 53.8, 46.7, 19.8, 7.9. ESI-HRMS (m/z): Calcd. for C$_6$H$_{13}$N$_4$O$_3$S [M+H]$^+$ 221.0703; found 221.0701.

N-(6-methyl-3-oxo-2,3-dihydro-1,2,4-triazin-4(5H)-yl)-n-propylsulfonamide (I$_a$-3)

White solid, yield is 73%, melting point is 177-178° C. $^1$H NMR (300 MHz, DMSO-d$_6$) δ 9.98 (s, 1H, NH), 9.81 (s, 1H, NH), 4.15 (s, 2H, CH$_2$), 3.07 (t, J=7.5 Hz, 2H, CH$_2$CH$_2$CH$_3$), 1.85 (s, 3H, CH$_3$), 1.73-1.80 (m, 2H, CH$_2$CH$_2$CH$_3$), 0.95 (t, J=7.5 Hz, 3H, CH$_2$CH$_2$CH$_3$); $^{13}$C NMR (100 MHz, DMSO-d$_6$) δ 151.2, 145.6, 53.8, 19.8, 16.7, 12.8. ESI-HRMS (m/z): Calcd. for C$_7$H$_{15}$N$_4$O$_3$S [M+H]$^+$ 235.0859; found 235.0856.

N-(6-methyl-3-oxo-2,3-dihydro-1,2,4-triazin-4(5H)-yl)-n-butylsulfonamide (I$_a$-4)

White solid, yield is 71%, melting point is 167-169° C. $^1$H NMR (300 MHz, DMSO-d$_6$) δ 9.99 (s, 1H, NH), 9.81 (s, 1H, NH), 4.15 (s, 2H, CH$_2$), 3.10 (t, J=7.5 Hz, 2H, CH$_2$CH$_2$CH$_2$CH$_3$), 1.85 (s, 3H, CH$_3$), 1.67-1.77 (m, 2H, CH$_2$CH$_2$CH$_2$CH$_3$), 1.30-1.40 (m, 2H, CH$_2$CH$_2$CH$_2$CH$_3$), 0.87 (t, J=7.2 Hz, 3H, CH$_2$CH$_2$CH$_2$CH$_3$); $^{13}$C NMR (100 MHz, DMSO-d$_6$) δ 151.2, 145.7, 53.8, 51.9, 24.9, 20.9, 19.8, 13.5. ESI-HRMS (m/z): Calcd. for C81117N$_4$O$_3$S [M+H]$^+$ 249.1016; found 249.1018.

N-(6-methyl-3-oxo-2,3-dihydro-1,2,4-triazin-4(5H)-yl)-cyclopropylsulfonamide (I$_a$-5)

White solid, yield is 64%, melting point is 146-148° C. $^1$H NMR (400 MHz, DMSO-d$_6$) δ 9.96 (s, 1H, NH), 9.79 (s, 1H, NH), 4.13 (s, 2H, CH$_2$), 2.57-2.63 (m, 1H, CH(CH$_2$)$_2$), 1.86 (s, 3H, CH$_3$), 0.93-0.98 (m, 4H, CH(CH$_2$)$_2$); $^{13}$C NMR (100 MHz, DMSO-d$_6$) δ 151.3, 145.6, 53.3, 29.9, 19.8, 5.4. ESI-HRMS (m/z): Calcd. for C$_7$H$_{13}$N$_4$O$_3$S [M+H]$^+$ 233.0703; found 233.0703.

N-(6-methyl-3-oxo-2,3-dihydro-1,2,4-triazin-4(5H)-yl)-cyclohexylsulfonamide (I$_a$-6)

White solid, yield is 43%, melting point is 166-168° C. $^1$H NMR (400 MHz, DMSO-d$_6$) δ 9.95 (s, 1H, NH), 9.73 (s, 1H, NH), 4.14 (s, 2H, CH$_2$), 2.99-3.06 (m, 1H), 1.85 (s, 3H, CH$_3$), 1.76-1.79 (m, 2H), 1.28-1.37 (m, 3H), 1.07-1.25 (m, 5H); $^{13}$C NMR (100 MHz, DMSO-d$_6$) δ 151.3, 145.6, 59.8, 53.9, 25.8, 24.8, 24.7, 19.8. ESI-HRMS (m/z): Calcd. for C$_{10}$H$_{18}$N$_4$O$_3$S [M+H]$^+$ 275.1172; found 275.1170.

N-(6-methyl-3-oxo-2,3-dihydro-1,2,4-triazin-4(5H)-yl)-phenylmethylsulfonamide (I$_a$-7)

White solid, yield is 78%, melting point is 189-190° C. $^1$H NMR (300 MHz, DMSO-d$_6$) δ 10.04 (s, 1H, NH), 9.86 (s, 1H, NH), 7.46-7.50 (m, 2H, Ar—H), 7.33-7.40 (m, 3H, Ar—H), 4.46 (s, 2H, CH$_2$), 4.13 (s, 2H, CH$_2$), 1.86 (s, 3H, $CH_3$); $^{13}C$ NMR (100 MHz, DMSO-$d_6$) δ 151.3, 145.6, 131.2, 129.4, 128.4, 128.2, 58.7, 53.8, 19.8. ESI-HRMS (m/z): Calcd. for $C_{11}H_{15}N_4O_3S$ [M+H]$^+$ 283.0859; found 283.0860.

N-(6-methyl-3-oxo-2,3-dihydro-1,2,4-triazin-4(5H)-yl)-naphthyl-1-sulfonamide ($I_a$-8)

White solid, yield is 72%, melting point is 174-175° C. $^1$H NMR (400 MHz, CDCl$_3$) δ 8.71 (d, J=8.4 Hz, 1H), 8.27 (d, J=7.2 Hz, 1H), 8.11 (d, J=8.4 Hz, 1H), 7.93 (d, J=8.0 Hz, 1H), 7.68 (t, J=7.2 Hz, 1H), 7.60 (t, J=8.0 Hz, 1H), 7.54 (t, J=7.6 Hz, 1H), 4.24 (s, 2H, CH$_2$), 1.98 (s, 3H, CH$_3$); $^{13}$C NMR (100 MHz, CDCl$_3$) δ 150.9, 146.7, 135.7, 134.1, 132.1, 131.4, 129.1, 128.6, 127.0, 124.3, 124.1, 52.5, 20.5. ESI-HRMS (m/z): Calcd. for $C_{14}H_{14}N_4O_3S$ [M+H]$^+$ 319.0859; found 319.0860.

N-(6-methyl-3-oxo-2,3-dihydro-1,2,4-triazin-4(5H)-yl)-benzenesulfonamide ($I_a$-9)

White solid, yield is 77%, melting point is 206-208° C. $^1$H NMR (400 MHz, DMSO-$d_6$) δ 10.23 (s, 1H, NH), 9.81 (s, 1H, NH), 7.80-7.82 (m, 2H, Ar—H), 7.64-7.67 (m, 1H, Ar—H), 7.54-7.58 (m, 2H, Ar—H), 4.05 (s, 2H, CH$_2$), 1.83 (s, 3H, CH$_3$); $^{13}$C NMR (100 MHz, DMSO-$d_6$) δ 150.7, 145.6, 138.8, 133.2, 128.9, 127.7, 52.7, 19.9. ESI-HRMS (m/z): Calcd. for $C_{10}H_{13}N_4O_3S$ [M+H]$^+$ 269.0703; found 269.0704.

2-methyl-N-(6-methyl-3-oxo-2,3-dihydro-1,2,4-triazin-4(5H)-yl)-benzenesulfonamide ($I_a$-10)

White solid, yield is 59%, melting point is 240-241° C. $^1$H NMR (400 MHz, DMSO-$d_6$) δ 10.15 (s, 1H, NH), 9.76 (s, 1H, NH), 7.84 (d, J=7.6 Hz, 1H, Ar—H), 7.51 (t, J=6.8 Hz, 1H, Ar—H), 7.31-7.37 (m, 2H, Ar—H), 4.03 (s, 2H, CH$_2$), 2.65 (s, 3H, CH$_3$), 1.81 (s, 3H, CH$_3$); $^{13}$C NMR (100 MHz, DMSO-$d_6$) δ 150.9, 145.6, 138.4, 136.9, 133.2, 132.2, 129.6, 125.8, 52.7, 20.2, 19.8. ESI-HRMS (m/z): Calcd. for $C_{11}H_{15}N_4O_3S$ [M+H]$^+$ 283.0859; found 283.0859.

3-methyl-N-(6-methyl-3-oxo-2,3-dihydro-1,2,4-triazin-4(5H)-yl)-benzenesulfonamide ($I_a$-11)

White solid, yield is 82%, melting point is 150-151° C. $^1$H NMR (400 MHz, DMSO-$d_6$) δ 10.16 (s, 1H, NH), 9.79 (s, 1H, NH), 7.60-7.63 (m, 2H, Ar—H), 7.42-7.46 (m, 2H, Ar—H), 4.03 (s, 2H, CH$_2$), 2.37 (s, 3H, CH$_3$), 1.82 (s, 3H, CH$_3$); $^{13}$C NMR (100 MHz, DMSO-$d_6$) δ 150.7, 145.6, 138.8, 138.5, 133.8, 128.7, 127.8, 124.9, 52.7, 20.8, 19.8. ESI-HRMS (m/z): Calcd. for $C_{11}H_{15}N_4O_3S$ [M+H]$^+$ 283.0859; found 283.0858.

4-methyl-N-(6-methyl-3-oxo-2,3-dihydro-1,2,4-triazin-4(5H)-yl)-benzenesulfonamide ($I_a$-12)

White solid, yield is 68%, melting point is 199-200° C. $^1$H NMR (300 MHz, DMSO-$d_6$) δ 10.10 (s, 1H, NH), 9.79 (s, 1H, NH), 7.69 (d, J=8.4 Hz, 2H, Ar—H), 7.36 (d, J=8.1 Hz, 2H, Ar—H), 4.05 (s, 2H, CH$_2$), 2.38 (s, 3H, CH$_3$), 1.83 (s, 3H, CH$_3$); $^{13}$C NMR (100 MHz, DMSO-$d_6$) δ 150.7, 145.7, 143.5, 135.9, 129.4, 127.8, 52.7, 21.1, 19.9. ESI-HRMS (m/z): Calcd. for $C_{11}H_{15}N_4O_3S$ [M+H]$^+$ 283.0859; found 283.0863.

2,4,6-trimethyl-N-(6-methyl-3-oxo-2,3-dihydro-1,2,4-triazin-4(5H)-yl)-benzenesulfonamide ($I_a$-13)

White solid, yield is 67%, melting point is 224-226° C. $^1$H NMR (400 MHz, DMSO-$d_6$) δ 9.91 (s, 1H, NH), 9.80 (s, 1H, NH), 6.99 (s, 2H, Ar—H), 4.01 (s, 2H, CH$_2$), 2.54 (s, 3H, CH$_3$), 2.24 (s, 3H, CH$_3$), 1.82 (s, 3H, CH$_3$); $^{13}$C NMR (100 MHz, DMSO-$d_6$) δ 151.2, 145.9, 142.2, 139.8, 133.0, 131.4, 52.3, 22.7, 20.5, 19.9. ESI-HRMS (m/z): Calcd. for $C_{13}H_{19}N_4O_3S$ [M+H]$^+$ 311.1172; found 311.1172.

4-methoxy-N-(6-methyl-3-oxo-2,3-dihydro-1,2,4-triazin-4(5H)-yl)-benzenesulfonamide ($I_a$-14)

White solid, yield is 68%, melting point is 245-246° C. $^1$H NMR (400 MHz, DMSO-$d_6$) δ 9.99 (s, 1H, NH), 9.78 (s, 1H, NH), 7.73 (d, J=8.8 Hz, 2H, Ar—H), 7.06 (d, J=8.8 Hz, 2H, Ar—H), 4.04 (s, 2H, CH$_2$), 3.82 (s, 3H, OCH$_3$), 1.83 (s, 3H, CH$_3$); $^{13}$C NMR (100 MHz, DMSO-$d_6$) δ 162.8, 150.7, 145.6, 130.1, 130.0, 114.1, 55.7, 52.6, 19.9. ESI-HRMS (m/z): Calcd. for $C_{11}H_{15}N_4O_4S$ [M+H]$^+$ 299.0809; found 299.0807.

4-tert-butyl-N-(6-methyl-3-oxo-2,3-dihydro-1,2,4-triazin-4(5H)-yl)-benzenesulfonamide ($I_a$-15)

White solid, yield is 59%, melting point is 240-241° C. $^1$H NMR (400 MHz, DMSO-$d_6$) δ 10.08 (s, 1H, NH), 9.85 (s, 1H, NH), 7.74 (d, J=8.0 Hz, 2H, Ar—H), 7.59 (d, J=8.0 Hz, 2H, Ar—H), 3.98 (s, 2H, CH$_2$), 1.80 (s, 3H, CH$_3$), 1.29 (s, 9H, C(CH$_3$)$_3$); $^{13}$C NMR (100 MHz, DMSO-$d_6$) δ 156.2, 150.9, 145.6, 136.2, 127.6, 125.8, 52.6, 34.9, 30.8, 19.8. ESI-HRMS (m/z): Calcd. for $C_{14}H_{21}N_4O_3S$ [M+H]$^+$ 325.1329; found 325.1329.

2-fluoro-N-(6-methyl-3-oxo-2,3-dihydro-1,2,4-triazin-4(5H)-yl)-benzenesulfonamide ($I_a$-16)

White solid, yield is 73%, melting point is 206-208° C. $^1$H NMR (400 MHz, DMSO-$d_6$) δ 10.49 (s, 1H, NH), 9.80 (s, 1H, NH), 7.79 (t, J=6.8 Hz, 1H, Ar—H), 7.67-7.72 (m, 1H, Ar—H), 7.39 (t, J=9.6 Hz, 1H, Ar—H), 7.33 (t, J=7.6 Hz, 1H, Ar—H), 4.13 (s, 2H, CH$_2$), 1.85 (s, 3H, CH$_3$); $^{13}$C NMR (100 MHz, DMSO-$d_6$) δ 159.2 (d, J=254.0 Hz), 150.6, 145.5, 135.9 (d, J=8.7 Hz), 130.2, 127.1 (d, J=14 Hz), 124.3 (d, J=3.2 Hz), 117.0 (d, J=20.9 Hz), 53.2, 19.8. ESI-HRMS (m/z): Calcd. for $C_{10}H_{12}FN_4O_3S$ [M+H]$^+$ 287.0609; found 287.0609.

3-fluoro-N-(6-methyl-3-oxo-2,3-dihydro-1,2,4-triazin-4(5H)-yl)-benzenesulfonamide ($I_a$-17)

White solid, yield is 81%, melting point is 180-181° C. $^1$H NMR (400 MHz, DMSO-$d_6$) δ 10.45 (s, 1H, NH), 9.83 (s, 1H, NH), 7.66 (d, J=8.0 Hz, 1H, Ar—H), 7.59-7.63 (m, 2H, Ar—H), 7.53 (t, J=8.4 Hz, 1H, Ar—H), 4.11 (s, 2H, CH$_2$), 1.85 (s, 3H, CH$_3$); $^{13}$C NMR (100 MHz, DMSO-$d_6$) δ 161.5 (d, J=246.1 Hz), 150.5, 145.6, 141.0 (d, J=7.0 Hz), 131.1 (d, J=7.7 Hz), 124.0 (d, J=2.7 Hz), 120.3 (d, J=20.9 Hz), 114.7 (d, J=24.3 Hz), 53.0, 19.8. ESI-HRMS (m/z): Calcd. for $C_{10}H_{12}FN_4O_3S$ [M+H]$^+$ 287.0609; found 287.0605.

4-fluoro-N-(6-methyl-3-oxo-2,3-dihydro-1,2,4-triazin-4(5H)-yl)-benzenesulfonamide ($I_a$-18)

White solid, yield is 65%, melting point is 216-217° C. $^1$H NMR (400 MHz, DMSO-$d_6$) δ 10.29 (s, 1H, NH), 9.81 (s, 1H, NH), 7.85-7.89 (m, 2H, Ar—H), 7.40 (t, J=8.8 Hz, 2H, Ar—H), 4.11 (s, 2H, CH$_2$), 1.85 (s, 3H, CH$_3$); $^{13}$C NMR (100 MHz, DMSO-d$_6$) δ 164.7 (d, J=249.9 Hz), 150.6, 145.7, 135.1 (d, J=2.7 Hz), 130.9 (d, J=9.7 Hz), 116.0 (d, J=22.6 Hz), 52.9, 19.9. ESI-HRMS (m/z): Calcd. for C$_{10}$H$_{12}$FN$_4$O$_3$S [M+H]$^+$ 287.0609; found 287.0606.

2,4-difluoro-N-(6-methyl-3-oxo-2,3-dihydro-1,2,4-triazin-4(5H)-yl)-benzenesulfonamide (I$_a$-19)

White solid, yield is 77%, melting point is 211-213° C. $^1$H NMR (400 MHz, DMSO-d$_6$) δ 10.59 (s, 1H, NH), 9.82 (s, 1H, NH), 7.81-7.87 (m, 1H, Ar—H), 7.50 (t, J=10.0 Hz, 1H, Ar—H), 7.21 (t, J=8.4 Hz, 1H, Ar—H), 4.14 (s, 2H, CH$_2$), 1.85 (s, 3H, CH$_3$); $^{13}$C NMR (100 MHz, DMSO-d$_6$) δ 165.5 (dd, J=12.5, 12.5 Hz), 160.2 (dd, J=14.1, 14.2 Hz), 150.6, 145.5, 132.4 (d, J=10.8 Hz), 123.9 (dd, J=4.4, 4.7 Hz), 111.7 (dd, J=4.1, 3.6 Hz), 105.7 (t, J=25.7 Hz), 53.3, 19.8. ESI-HRMS (m/z): Calcd. for C$_{10}$H$_{11}$F$_2$N$_4$O$_3$S [M+H]$^+$ 305.0514; found 305.0511.

2,3,4-trifluoro-N-(6-methyl-3-oxo-2,3-dihydro-1,2,4-triazin-4(5H)-yl)-benzenesulfonamide (I$_a$-20)

White solid, yield is 71%, melting point is 214-216° C. $^1$H NMR (400 MHz, DMSO-d$_6$) δ 10.88 (s, 1H, NH), 9.89 (s, 1H, NH), 7.66-7.71 (m, 1H, Ar—H), 7.45-7.51 (m, 1H, Ar—H), 4.18 (s, 2H, CH$_2$), 1.87 (s, 3H, CH$_3$); $^{13}$C NMR (100 MHz, DMSO-d$_6$) δ 153.6 (dd, J=10.6, 9.5 Hz), 150.7, 148.9 (dd, J=8.5, 8.1 Hz), 145.7, 140.8 (t, J=15.6 Hz), 138.3 (t, J=15.3 Hz), 125.3 (m), 112.6 (dd, J=2.6, 2.6 Hz), 53.4, 19.8. ESI-HRMS (m/z): Calcd. for C$_{10}$H$_{10}$F$_3$N$_4$O$_3$S [M+H]$^+$ 323.0420; found 323.0414.

4-chloro-N-(6-methyl-3-oxo-2,3-dihydro-1,2,4-triazin-4(5H)-yl)-benzenesulfonamide (I$_a$-21)

White solid, yield is 74%, melting point is 214-215° C. $^1$H NMR (400 MHz, DMSO-d$_6$) δ 10.38 (s, 1H, NH), 9.82 (s, 1H, NH), 7.80 (d, J=8.4 Hz, 2H, Ar—H), 7.63 (d, J=8.4 Hz, 2H, Ar—H), 4.12 (s, 2H, CH$_2$), 1.85 (s, 3H, CH$_3$); $^{13}$C NMR (100 MHz, DMSO-d$_6$) δ 150.5, 145.6, 138.1, 137.7, 129.7, 129.0, 53.0, 19.9. ESI-HRMS (m/z): Calcd. for C$_{10}$H$_{12}$C$_1$N$_4$O$_3$S [M+H]$^+$ 303.0313; found 303.0316.

4-bromo-N-(6-methyl-3-oxo-2,3-dihydro-1,2,4-triazin-4(5H)-yl)-benzenesulfonamide (I$_a$-22)

White solid, yield is 75%, melting point is 230-232° C. $^1$H NMR (400 MHz, DMSO-d$_6$) δ 10.40 (s, 1H, NH), 9.84 (s, 1H, NH), 7.79 (d, J=8.4 Hz, 2H, Ar—H), 7.73 (d, J=8.4 Hz, 2H, Ar—H), 4.13 (s, 2H, CH$_2$), 1.86 (s, 3H, CH$_3$); $^{13}$C NMR (100 MHz, DMSO-d$_6$) δ 150.6, 145.7, 138.1, 132.0, 129.8, 127.2, 53.0, 19.9. ESI-HRMS (m/z): Calcd. for C$_{10}$H$_{12}$BrN$_4$O$_3$S [M+H]$^+$ 346.9808; found 346.9804.

4-iodo-N-(6-methyl-3-oxo-2,3-dihydro-1,2,4-triazin-4(5H)-yl)-benzenesulfonamide (I$_a$-23)

White solid, yield is 81%, melting point is 241-243° C. $^1$H NMR (400 MHz, DMSO-d$_6$) δ 10.36 (s, 1H, NH), 9.84 (s, 1H, NH), 7.95 (d, J=8.4 Hz, 2H, Ar—H), 7.56 (d, J=8.4 Hz, 2H, Ar—H), 4.11 (s, 2H, CH$_2$), 1.85 (s, 3H, CH$_3$); $^{13}$C NMR (100 MHz, DMSO-d$_6$) δ 150.5, 145.6, 138.5, 137.7, 129.4, 101.5, 52.9, 19.8. ESI-HRMS (m/z): Calcd. for C$_{10}$H$_{12}$IN$_4$O$_3$S [M+H]$^+$ 394.9669; found 394.9666.

N-(4-(N-(6-methyl-3-oxo-2,3-dihydro-1,2,4-triazin-4(5H)-yl)sulfamyl)phenyl)acetamide (I$_a$-24)

White solid, yield is 65%, melting point is 255-257° C. $^1$H NMR (300 MHz, DMSO-d$_6$) δ 10.32 (s, 1H, NH), 10.02 (s, 1H, NH), 9.77 (s, 1H, NH), 7.72 (brs, 4H), 4.05 (s, 2H, CH$_2$), 2.08 (s, 3H, CH$_3$), 1.83 (s, 3H, CH$_3$); $^{13}$C NMR (100 MHz, DMSO-d$_6$) δ 169.1, 150.7, 145.6, 143.5, 132.0, 129.0, 118.2, 52.6, 24.2, 19.9. ESI-HRMS (m/z): Calcd. for C$_{12}$H$_{16}$N$_5$O$_4$S [M+H]$^+$ 326.0918; found 326.0921.

4-cyano-N-(6-methyl-3-oxo-2,3-dihydro-1,2,4-triazin-4(5H)-yl)-benzenesulfonamide (I$_a$-25)

White solid, yield is 65%, melting point is 256-257° C. $^1$H NMR (400 MHz, DMSO-d$_6$) δ 10.66 (s, 1H, NH), 9.85 (s, 1H, NH), 8.06 (d, J=8.0 Hz, 2H, Ar—H), 7.97 (d, J=8.0 Hz, 2H, Ar—H), 4.15 (s, 2H, CH$_2$), 1.86 (s, 3H, CH$_3$); $^{13}$C NMR (100 MHz, DMSO-d$_6$) δ 150.5, 145.7, 143.2, 132.9, 128.5, 117.7, 115.4, 53.2, 19.8. ESI-HRMS (m/z): Calcd. for C$_{11}$H$_{12}$IN$_5$O$_3$S [M+H]$^+$ 294.0655; found 294.0659.

N-(6-methyl-3-oxo-2,3-dihydro-1,2,4-triazin-4(5H)-yl)-4-(trifluoromethyl)-benzenesulfonamide (I$_a$-26)

White solid, yield is 74%, melting point is 243-244° C. $^1$H NMR (400 MHz, DMSO-d$_6$) δ 10.59 (s, 1H, NH), 9.86 (s, 1H, NH), 8.02 (d, J=8.4 Hz, 2H, Ar—H), 7.95 (d, J=8.4 Hz, 2H, Ar—H), 4.15 (s, 2H, CH$_2$), 1.86 (s, 3H, CH$_3$); $^{13}$C NMR (100 MHz, DMSO-d$_6$) δ 150.6, 145.7, 143.0, 132.7 (q, J=32 Hz), 128.8, 126.0 (q, J=4.3 Hz), 123.6 (q, J=271.2 Hz), 53.2, 19.9. ESI-HRMS (m/z): Calcd. for C$_{11}$H$_{12}$F$_3$N$_4$O$_3$S [M+H]$^+$ 337.0577; found 337.0577.

N-(6-methyl-3-oxo-2,3-dihydro-1,2,4-triazin-4(5H)-yl)-4-(trifluoromethoxy)-benzenesulfonamide (I$_a$-27)

White solid, yield is 70%, melting point is 215-216° C. $^1$H NMR (400 MHz, DMSO-d$_6$) δ 10.43 (s, 1H, NH), 9.85 (s, 1H, NH), 7.94 (d, J=8.4 Hz, 2H, Ar—H), 7.55 (d, J=8.4 Hz, 2H, Ar—H), 4.12 (s, 2H, CH$_2$), 1.85 (s, 3H, CH$_3$); $^{13}$C NMR (100 MHz, DMSO-d$_6$) δ 151.4, 150.6, 145.7, 137.9, 130.5, 120.9, 119.9 (q, J=257.7 Hz), 53.1, 19.8. ESI-HRMS (m/z): Calcd. for C$_{11}$H$_{12}$F$_3$N$_4$O$_4$S [M+H]$^+$ 353.0526; found 353.0525.

N-(6-methyl-3-oxo-2,3-dihydro-1,2,4-triazin-4(5H)-yl)-thienyl-2-sulfonamide (I$_a$-28)

White solid, yield is 69%, melting point is 191-193° C. $^1$H NMR (400 MHz, DMSO-d$_6$) δ 10.33 (s, 1H, NH), 9.87 (s, 1H, NH), 7.99 (d, J=5.2 Hz, 1H, Ar—H), 7.63 (d, J=3.6 Hz, 1H, Ar—H), 7.17 (t, J=4.0 Hz, 1H, Ar—H), 4.04 (s, 2H, CH$_2$), 1.84 (s, 3H, CH$_3$); $^{13}$C NMR (100 MHz, DMSO-d$_6$) δ 150.8, 145.7, 138.7, 134.5, 133.7, 127.7, 52.6, 20.0. ESI-HRMS (m/z): Calcd. for C$_8$H$_{11}$N$_4$O$_3$S$_2$[M+H]$^+$ 275.0267; found 275.0262.

N-(6-methyl-3-oxo-2,3-dihydro-1,2,4-triazin-4(5H)-yl)-thienyl-3-sulfonamide (I$_a$-29)

White solid, yield is 42%, melting point is 214-215° C. $^1$H NMR (400 MHz, DMSO-d$_6$) δ 10.14 (s, 1H, NH), 9.85 (s, 1H, NH), 8.25 (s, 1H, Het-H), 7.71 (d, J=2.4 Hz, 1H, Het-H), 7.31 (d, J=4.8 Hz, 1H, Het-H), 4.03 (s, 2H, CH$_2$), 1.83 (s, 3H, CH$_3$); $^{13}$C NMR (100 MHz, DMSO-d$_6$) δ 150.8, 145.6, 141.0, 138.4, 132.7, 128.5, 126.1, 52.6, 19.9. ESI-HRMS (m/z): Calcd. for $C_8H_{10}N_4O_3S_2$ [M+H]$^+$ 275.0267; found 275.0272.

3,5-dimethyl-N-(6-methyl-3-oxo-2,3-dihydro-1,2,4-triazin-4(5H)-yl)-isoxazolyl-4-sulfonamide ($I_a$-30)

Colorless oily liquid, yield is 35%. $^1$H NMR (400 MHz, DMSO-d$_6$) δ 10.55 (s, 1H, NH), 9.96 (s, 1H, NH), 4.17 (s, 2H, CH$_2$), 2.53 (s, 3H, CH$_3$), 2.32 (s, 3H, CH$_3$), 1.88 (s, 3H, CH$_3$); $^{13}$C NMR (100 MHz, DMSO-d$_6$) δ 173.8, 157.9, 150.7, 146.1, 114.7, 52.9, 19.9, 12.2, 10.5. ESI-HRMS (m/z): Calcd. for $C_9H_{13}N_5O_4S$ [M+H]$^+$ 288.0761; found 288.0759.

1-methyl-N-(6-methyl-3-oxo-2,3-dihydro-1,2,4-triazin-4(5H)-yl)-1H-imidazolyl-4-sulfonamide ($I_a$-31)

Yellow solid, yield is 43%, melting point is 188-190° C. $^1$H NMR (400 MHz, DMSO-d$_6$) δ 9.85 (s, 1H, NH), 9.84 (s, 1H, NH), 7.88 (s, 1H, Het-H), 7.85 (s, 1H, Het-H), 3.98 (s, 2H, CH$_2$), 3.75 (s, 3H, CH$_3$), 1.84 (s, 3H, CH$_3$); $^{13}$C NMR (100 MHz, DMSO-d$_6$) δ 151.2, 145.3, 139.8, 137.9, 125.9, 52.1, 33.5, 19.7. ESI-HRMS (m/z): Calcd. for $C_8H_{12}N_6O_3S$ [M+H]$^+$ 273.0764; found 273.0766.

1,2-dimethyl-N-(6-methyl-3-oxo-2,3-dihydro-1,2,4-triazin-4(5H)-yl)-1H-imidazolyl-4-sulfonamide ($I_a$-32)

Yellow solid, yield is 47%, melting point is 180-182° C. $^1$H NMR (400 MHz, DMSO-d$_6$) δ 10.55 (s, 1H, NH), 9.95 (s, 1H, NH), 8.14 (s, 1H, Het-H), 4.08 (s, 2H, CH$_2$), 3.71 (s, 3H, CH$_3$), 3.16 (s, 3H, CH$_3$), 1.84 (s, 3H, CH$_3$); $^{13}$C NMR (100 MHz, DMSO-d$_6$) δ 151.1, 147.7, 145.7, 127.0, 120.4, 52.9, 34.0, 19.9, 11.4. ESI-HRMS (m/z): Calcd. for $C_9H_{14}N_6O_3S$ [M+H]$^+$ 287.0921; found 287.0927.

N-(6-methyl-3-oxo-2,3-dihydro-1,2,4-triazin-4(5H)-yl)-2,3-dihydrobenzofuran-5-sulfonamide ($I_a$-33)

White solid, yield is 43%, melting point is 263-264° C. $^1$H NMR (400 MHz, DMSO-d$_6$) δ 9.95 (s, 1H, NH), 9.80 (s, 1H, NH), 7.65 (s, 1H, Ar—H), 7.56 (d, J=8.4 Hz, 1H, Ar—H), 6.88 (d, J=8.4 Hz, 1H, Ar—H), 4.64 (t, J=8.4 Hz, 2H), 4.04 (s, 2H, CH$_2$), 3.22 (t, J=8.8 Hz, 2H), 1.83 (s, 3H, CH$_3$); $^{13}$C NMR (100 MHz, DMSO-d$_6$) δ 163.6, 150.8, 145.6, 130.0, 129.4, 128.3, 125.2, 108.8, 72.2, 52.6, 28.4, 19.9. ESI-HRMS (m/z): Calcd. for $C_{12}H_{14}N_4O_4S$ [M+H]$^+$ 311.0809; found 331.0812.

N-(6-methyl-3-oxo-2,3-dihydro-1,2,4-triazin-4(5H)-yl)-2,3-dihydrobenzo[b][1,4]dioxin-6-sulfonamide ($I_a$-34)

White solid, yield is 36%, melting point is 213-214° C. $^1$H NMR (400 MHz, DMSO-d$_6$) δ 10.06 (s, 1H, NH), 9.83 (s, 1H, NH), 7.27 (q, J=2.0 Hz, 1H, Ar—H), 7.25 (d, J=2.0 Hz, 1H, Ar—H), 7.00 (d, J=8.4 Hz, 1H, Ar—H), 4.32 (d, J=5.2 Hz, 2H, OCH$_2$), 4.29 (d, J=5.2 Hz, 2H, OCH$_2$), 4.03 (s, 2H, CH$_2$), 1.83 (s, 3H, CH$_3$); $^{13}$C NMR (100 MHz, DMSO-d$_6$) δ 150.7, 147.5, 145.6, 143.0, 131.0, 121.5, 117.3, 116.9, 64.5, 64.0, 52.6, 19.9. ESI-HRMS (m/z): Calcd. for $C_{12}H_{14}N_4O_5S$ [M+H]$^+$ 327.0758; found 327.0760.

Example 2

(1) Synthesis of Compound $I_b$-1

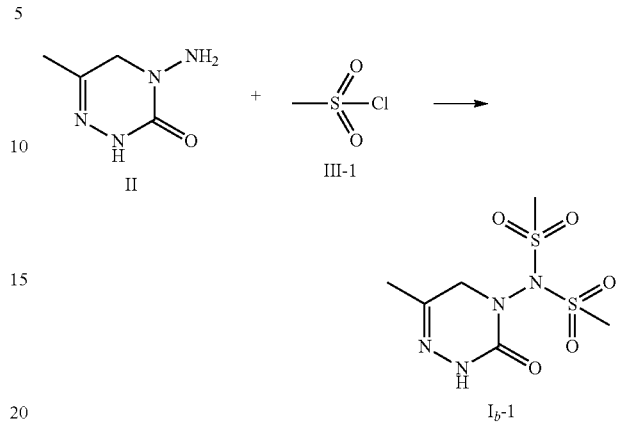

Synthesis of N-(6-methyl-3-oxo-2,3-dihydro-1,2,4-triazin-4(5H)-yl)-N-(methylsulfonyl)-methylsulfonylamide ($I_b$-1)

Amino-triazinone (0.26 g, 2 mmol) and pyridine (30 mL) are added into a 100 mL single-neck flask, and are stirred to dissolve, then methylsulfonyl chloride (0.55 g, 4.8 mmol) is added into the flask, and the mixture is stirred and held overnight at room temperature, the reaction is monitored with a TLC till it is finished. After desolvation of the reaction liquid under reduced pressure, water is added to the mixture and the product is extracted with methylene chloride and then washed twice with saturated sodium chloride solution and dried with sodium sulfate; next, the product is treated by chromatography in a silica-gel column with methylene chloride/methanol (150:1-130:1); thus, 0.48 g white solid is obtained, the yield is 85%, and the melting point of the white solid is 220-222° C. $^1$H NMR (400 MHz, DMSO-d$_6$) δ 10.34 (s, 1H, NH), 4.39 (s, 2H, CH$_2$), 3.56 (s, 6H, CH$_3$), 1.89 (s, 3H, CH$_3$); $^{13}$C NMR (100 MHz, DMSO-d$_6$) δ 149.9, 146.0, 54.3, 44.8, 19.7. ESI-HRMS (m/z): Calcd. for $C_6H_{13}N_4O_5S_2$ [M+H]$^+$ 285.0322; found 285.0323.

(2) Synthesis of Compounds $I_b$-2~$I_b$-9 by repeating the steps for $I_b$-1

Except:
In the preparation of the compound $I_b$-2, the methylsulfonyl chloride is replaced with ethylsulfonyl chloride (from Energy Chemical Co., Ltd.) in the same molar mass;
In the preparation of the compound $I_b$-3, the methylsulfonyl chloride is replaced with n-propylsulfonyl chloride (from Beijing Innochem Science & Technology Co., Ltd.) in the same molar mass; In the preparation of the compound $I_b$-4, the methylsulfonyl chloride is replaced with n-butylsulfonyl chloride (from Beijing Innochem Science & Technology Co., Ltd.) in the same molar mass;
In the preparation of the compound $I_b$-5, the methylsulfonyl chloride is replaced with

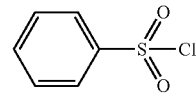

(from Tianjin Reagents Co., Ltd.) in the same molar mass;

In the preparation of the compound $I_b$-6, the methylsulfonyl chloride is replaced with

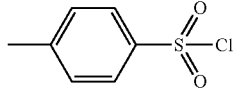

(from Shanghai Aladdin Bio-ChemBiochemical Technology Co., LTD) in the same molar mass;

In the preparation of the compound $I_b$-7, the methylsulfonyl chloride is replaced with

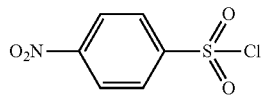

(from Shanghai Aladdin Bio-Chem Technology Co., LTD) in the same molar mass;

In the preparation of the compound $I_b$-8, the methylsulfonyl chloride is replaced with

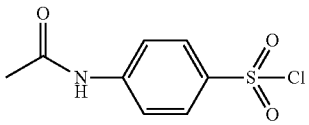

(from Shanghai Boka Chemical Technology Co., Ltd.) in the same molar mass;

In the preparation of the compound $I_b$-9, the methylsulfonyl chloride is replaced with

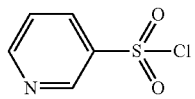

(from Beijing Innochem Science & Technology Co., Ltd.) in the same molar mass;

The obtained compounds are characterized as follows:

n-(ethylsulfonyl)-N-(6-methyl-3-oxo-2,3-dihydro-1,2,4-triazin-4(5H)-yl)-ethylsulfonamide ($I_b$-2)

White solid, yield is 74%, melting point is 183-184° C. $^1$H NMR (300 MHz, DMSO-$d_6$) δ 10.33 (s, 1H, NH), 4.31 (s, 2H, $CH_2$), 3.64 (q, J=7.5 Hz, 4H, $CH_2CH_3$), 1.89 (s, 3H, $CH_3$), 1.33 (t, J=9.6 Hz, 6H, $CH_2CH_3$); $^{13}$C NMR (100 MHz, DMSO-$d_6$) δ 150.1, 146.1, 54.0, 51.3, 19.8, 7.6. ESI-HRMS (m/z): Calcd. for $C_8H_{117}N_4O_5S_2[M+H]^+$ 313.0635; found 313.0633.

N-(6-methyl-3-oxo-2,3-dihydro-1,2,4-triazin-4(5H)-yl)-N-(n-propylsulfonyl)propyl-1-sulfonamide ($I_b$-3)

White solid, yield is 84%, melting point is 177-178° C. $^1$H NMR (300 MHz, DMSO-$d_6$) δ 10.32 (s, 1H, NH), 4.33 (s, 2H, $CH_2$), 3.54-3.69 (m 4H, $CH_2CH_2CH_3$), 1.89 (s, 3H, $CH_3$), 1.77-1.86 (m, 4H, $CH_2CH_2CH_3$), 1.00 (t, J=7.5 Hz, 6H, $CH_2CH_2CH_3$); $^{13}$C NMR (100 MHz, DMSO-$d_6$) δ 150.1, 146.0, 58.2, 54.1, 19.8, 16.5, 12.5. ESI-HRMS (m/z): Calcd. for $C_{10}H_{21}N_4O_5S_2[M+H]^+$ 341.0948; found 341.0946.

N-(n-butylsulfonyl)-N-(6-methyl-3-oxo-2,3-dihydro-1,2,4-triazin-4(5H)-yl)-butyl-1-sulfonamide ($I_b$-4)

White solid, yield is 85%, melting point is 157-158° C. $^1$H NMR (300 MHz, DMSO-$d_6$) δ 10.33 (s, 1H, NH), 4.33 (s, 2H, $CH_2$), 3.56-3.72 (m, 4H, $CH_2CH_2CH_2H_3$), 1.90 (s, 3H, $CH_3$), 1.71-1.83 (m, 4H, $CH_2CH_2CH_2H_3$), 1.38-1.46 (m, 4H, $CH_2CH_2CH_2H_3$), 0.9 (t, J=7.2 Hz, 6H, $CH_2CH_2CH_2CH_3$); $^{13}$C NMR (100 MHz, DMSO-$d_6$) δ 150.1, 146.0, 56.4, 54.1, 24.5, 20.7, 19.8, 13.3. ESI-HRMS (m/z): Calcd. for $C_{12}H_{25}N_4O_5S_2[M+H]^+$ 369.1261; found 369.1263.

N-(6-methyl-3-oxo-2,3-dihydro-1,2,4-triazin-4(5H)-yl)-N-(benzenesulfonyl)-benzenesulfonamide ($I_b$-5)

White solid, yield is 83%, melting point is 227-228° C. $^1$H NMR (400 MHz, DMSO-$d_6$) δ 10.25 (s, 1H, NH), 7.90 (d, J=7.5 Hz, 4H, Ar—H), 7.83 (t, J=7.5 Hz, 2H, Ar—H), 7.68 (t, J=7.8 Hz, 4H, Ar—H), 4.22 (s, 2H, $CH_2$), 1.87 (s, 3H, $CH_3$); $^{13}$C NMR (100 MHz, DMSO-$d_6$) δ 149.5, 146.3, 137.6, 135.1, 129.5, 128.6, 53.1, 19.9. ESI-HRMS (m/z): Calcd. for $C_{16}H_{17}N_4O_5S_2[M+H]^+$ 409.0635; found 409.0639.

4-methyl-N-(6-methyl-3-oxo-2,3-dihydro-1,2,4-triazin-4(5H)-yl)-N-(4-methylbenzenesulfonyl)benzenesulfonamide ($I_b$-6)

Straw yellow solid, yield is =81%, melting point is 219-220° C. $^1$H NMR (300 MHz, DMSO-$d_6$) δ 10.22 (s, 1H, NH), 7.77 (d, J=8.1 Hz, 4H, Ar—H), 7.47 (d, J=8.1 Hz, 4H, Ar—H), 4.20 (s, 2H, $CH_2$), 2.44 (s, 6H, $CH_3$), 1.87 (s, 3H, $CH_3$); $^{13}$C NMR (100 MHz, DMSO-$d_6$) δ 149.5, 146.3, 145.9, 134.8, 129.8, 128.7, 53.0, 21.2, 19.9. ESI-HRMS (m/z): Calcd. for $C_{18}H_{21}N_4O_5S_2[M+H]^+$ 437.0948; found 437.0947.

N-(6-methyl-3-oxo-2,3-dihydro-1,2,4-triazin-4(5H)-yl)-4-nitro-N-(4-nitrobenzenesulfonyl)-benzenesulfonamide ($I_b$-7)

Straw yellow solid, yield is 79%, melting point is 239-240° C. $^1$H NMR (300 MHz, DMSO-$d_6$) δ 10.37 (s, 1H, NH), 8.49 (d, J=9.0 Hz, 4H, Ar—H), 8.20 (d, J=9.0 Hz, 4H, Ar—H), 4.41 (s, 2H, $CH_2$), 1.93 (s, 3H, $CH_3$); $^{13}$C NMR (100 MHz, DMSO-$d_6$) δ 151.1, 149.1, 146.4, 142.3, 130.6, 124.8, 53.6, 19.9. ESI-HRMS (m/z): Calcd. for $C_{16}H_{15}N_6O_9S_2[M+H]^+$ 499.0336; found 499.0329.

4-acetamido-N-(6-methyl-3-oxo-2,3-dihydro-1,2,4-triazin-4(5H)-yl)-N-(4-acetamidobenzenesulfonyl)-benzenesulfonamide ($I_b$-8)

Straw yellow solid, yield is 78%, melting point is 188-190° C. $^1$H NMR (300 MHz, DMSO-$d_6$) δ 10.51 (s, 2H, NH), 10.18 (s, 1H, NH), 7.80 (s, 8H, Ar—H), 4.20 (s, 2H, $CH_2$), 2.12 (s, 6H, $CH_3$), 1.87 (s, 3H, $CH_3$); $^{13}$C NMR (100 MHz, DMSO-$d_6$) δ 169.4, 149.5, 146.2, 144.9, 130.6, 130.1, 118.3, 53.1, 24.3, 19.9. ESI-HRMS (m/z): Calcd. for $C_{20}H_{23}N_6O_7S_2[M+H]^+$ 540.1330; found 540.1332.

N-(6-methyl-3-oxo-2,3-dihydro-1,2,4-triazin-4(5H)-yl)-N-(pyrid-3-yl-sulfonyl)pyridyl-3-sulfonamide ($I_b$-9)

White solid, yield is 42%, melting point is 213-214° C. $^1$H NMR (400 MHz, CDCl$_3$) δ 9.05 (s, 2H, Py-H), 8.90 (d, J=4 Hz, 2H, Py-H), 8.18-8.21 (m, 2H, Py-H), 7.51 (s, 1H, NH), 7.49 (d, J=3 Hz, 2H, Py-H), 4.47 (s, 2H, CH2$_3$), 2.03 (s, 3H, CH$_3$); $^{13}$C NMR (100 MHz, CDCl$_3$) δ 155.2, 149.9, 149.4, 146.5, 137.1, 134.5, 123.8, 54.8, 20.4. ESI-HRMS (m/z): Calcd. for C$_{14}$H$_{14}$N$_6$O$_5$S$_2$ [M+H]$^+$ 411.0540; found 411.0534.

Example 3: Test of Insecticidal Activity Against Aphides, Through the Following Testing Procedure Test of Insecticidal Activity Against Aphides The insecticidal activity against aphides is tested through the following steps: the tested aphides are bean aphides (*Aphis laburni* Kaltenbach), a normal colony fed with broad bean leaves in a laboratory. The pesticide is weighed, 1 mL DMF is added to dissolve the pesticide, then two drops of emulsifier, Tween-20 are added, and distilled water is added in an appropriate amount; the mixture is stirred to a homogeneous state to prepare pesticide solution at required concentration (see the following table for the specific concentration). Broad bean leaves with aphides (about 60 aphides) are immersed in the reagent for 5 s, and then are taken out and swung gently to dry them, the residual reagent is absorbed with filter papers, then the broad bean twigs are inserted into a piece of water absorption sponge, and covered in a glass cover, and the opening is sealed with gauze; the result is checked after 96 h; the operations are repeated for 3 times for each compound. In a control group, only emulsifier and solvent are added into distilled water, and the mixture is stirred to a homogeneous state.

TABLE 1

Test Results of Insecticidal Activity of Pymetrozine and the Sulfonyl-Structure-Containing Triazinone Derivatives against Aphides

| No. | Mortalities (%) | | | | |
| --- | --- | --- | --- | --- | --- |
|     | 600 mg/kg | 100 mg/kg | 10 mg/kg | 5 mg/kg | 2.5 mg/kg |
| Pymetrozine | 100 | 100 | 90 | 30 | 0 |
| $I_a$-1 | 100 | 100 | 100 | 25 | — |
| $I_a$-2 | 100 | 90 | 50 | — | — |
| $I_a$-3 | 95 | 75 | 40 | — | — |
| $I_a$-4 | 85 | 70 | 20 | — | — |
| $I_a$-5 | 100 | 85 | 30 | — | — |
| $I_a$-6 | 85 | 45 | — | — | — |
| $I_a$-7 | 100 | 75 | 20 | — | — |
| $I_a$-8 | 90 | 85 | 25 | — | — |
| $I_a$-9 | 100 | 100 | 100 | 30 | — |
| $I_a$-10 | 100 | 100 | 100 | 90 | 25 |
| $I_a$-11 | 100 | 100 | 100 | 80 | 15 |
| $I_a$-12 | 100 | 100 | 100 | 100 | 30 |
| $I_a$-13 | 100 | 100 | 100 | 60 | 10 |
| $I_a$-14 | 100 | 100 | 100 | 100 | 35 |
| $I_a$-15 | 100 | 100 | 100 | 85 | 10 |
| $I_a$-16 | 100 | 100 | 90 | 30 | — |
| $I_a$-17 | 100 | 100 | 85 | 35 | — |
| $I_a$-18 | 100 | 100 | 100 | 45 | — |
| $I_a$-19 | 100 | 100 | 85 | 25 | — |
| $I_a$-20 | 100 | 100 | 70 | 10 | — |
| $I_a$-21 | 100 | 100 | 85 | 35 | — |
| $I_a$-22 | 100 | 100 | 100 | 40 | — |
| $I_a$-23 | 100 | 100 | 100 | 45 | — |
| $I_a$-24 | 100 | 95 | 75 | 10 | — |
| $I_a$-25 | 100 | 100 | 85 | 20 | — |
| $I_a$-26 | 100 | 100 | 100 | 30 | — |
| $I_a$-27 | 100 | 100 | 100 | 35 | — |
| $I_a$-28 | 100 | 100 | 65 | — | — |
| $I_a$-29 | 95 | 85 | 30 | — | — |
| $I_a$-30 | 95 | 45 | — | — | — |
| $I_a$-31 | 100 | 100 | 35 | — | — |
| $I_a$-32 | 100 | 100 | 30 | — | — |
| $I_a$-33 | 90 | 40 | — | — | — |
| $I_a$-34 | 90 | 35 | — | — | — |
| $I_b$-1 | 100 | 100 | 100 | 20 | — |
| $I_b$-2 | 85 | — | — | — | — |
| $I_b$-3 | 75 | — | — | — | — |
| $I_b$-4 | 90 | — | — | — | — |
| $I_b$-5 | 100 | 90 | 50 | 10 | — |
| $I_b$-6 | 100 | 80 | 30 | — | — |
| $I_b$-7 | 100 | 85 | 25 | — | — |
| $I_b$-8 | 90 | 50 | — | — | — |
| $I_b$-9 | 95 | 80 | 20 | — | — |

$^a$not measured.

As seen from Table 1: at a concentration of 10 mg/kg, a portion of the sulfonyl-structure-containing triazinone derivatives exhibit outstanding insecticidal activity against aphides, whose mortality is up to 100%. At a concentration of 5 mg/kg, $I_a$-1, $I_a$-9, $I_a$-16, $I_a$-17, $I_a$-18, $I_a$-19, $I_a$-21, $I_a$-22, $I_a$-23, $I_a$-25, $I_a$-26, $I_a$-27, and $I_b$-1 exhibit insecticidal activity equivalent to the insecticidal activity of pymetrozine against aphides respectively. Especially, the compounds $I_a$-10, $I_a$-11, $I_a$-12, $I_a$-13, $I_a$-14, and $I_a$-15 still exhibit insecticidal activity with mortalities of 25%, 15%, 30%, 10%, 35%, and 10% respectively at a concentration of 2.5 mg/kg, while pymetrozine has no insecticidal activity at the same concentration.

Example 4: Test of Insecticidal Activity Against Mosquito Larvae, Through the Following Testing Procedure Test of Insecticidal Activity Against Mosquito Larvae Method of testing against mosquito larvae: the tested mosquito larvae are Culer *pipiens pallens*, a normal colony fed indoor. About 5 mg compound to be tested is weighed and loaded into a penicillin vial, 5 mL acetone (or an appropriate solvent) is added into the vial, and the vial is oscillated to dissolve the compound; thus, 1,000 ppm mother liquid is obtained. 1 mL mother liquid is weighed and added into a 100 mL beaker filled with 89 mL water, 10 mosquito larvae in the early stage of the 4$^{th}$ instar together with 10 mL feeding solution are poured into the beaker; thus, the concentration of the pesticide solution is 10 ppm (the pesticide solutions with other concentrations are attained by diluting the mother liquid by corresponding times). The pesticide solution is placed in a standard treatment chamber, and the result is checked after 24 h. Water solution that contains 0.5 mL test solvent is used as a blank sample.

TABLE 2

Test Results of Insecticidal Activity of Pymetrozine
and the Sulfonyl-Structure-Containing Triazinone
Derivatives against Mosquito Larvae

| No. | Mortalities (%) | | | | |
|---|---|---|---|---|---|
| | 10 mg/kg | 5 mg/kg | 2 mg/kg | 1 mg/kg | 0.5 mg/kg |
| Pymetrozine | 100 | 40 | — | — | — |
| $I_a$-1 | 55 | — | — | — | — |
| $I_a$-2 | 20 | — | — | — | — |
| $I_a$-3 | 55 | — | — | — | — |
| $I_a$-4 | 20 | — | — | — | — |
| $I_a$-5 | 10 | — | — | — | — |
| $I_a$-6 | 70 | — | — | — | — |
| $I_a$-7 | 70 | — | — | — | — |
| $I_a$-8 | 15 | — | — | — | — |
| $I_a$-9 | 100 | 80 | 10 | — | — |
| $I_a$-10 | 100 | 100 | 40 | — | — |
| $I_a$-11 | 100 | 100 | 20 | — | — |
| $I_a$-12 | 100 | 100 | 10 | — | — |
| $I_a$-13 | 100 | 100 | 20 | — | — |
| $I_a$-14 | 100 | 95 | 10 | — | — |
| $I_a$-15 | 100 | 100 | 40 | — | — |
| $I_a$-16 | 100 | 100 | 30 | — | — |
| $I_a$-17 | 100 | 100 | 60 | — | — |
| $I_a$-18 | 100 | 100 | 40 | — | — |
| $I_a$-19 | 100 | 100 | 100 | 60 | — |
| $I_a$-20 | 100 | 100 | 20 | — | — |
| $I_a$-21 | 100 | 100 | 40 | — | — |
| $I_a$-22 | 100 | 100 | 100 | 100 | 40 |
| $I_a$-23 | 100 | 100 | 100 | 30 | — |
| $I_a$-24 | 100 | 45 | — | — | — |
| $I_a$-25 | 100 | 100 | 40 | — | — |
| $I_a$-26 | 100 | 100 | 100 | 20 | — |
| $I_a$-27 | 100 | 90 | 20 | — | — |
| $I_a$-28 | 100 | 20 | — | — | — |
| $I_a$-29 | 35 | — | — | — | — |
| $I_a$-30 | 35 | — | — | — | — |
| $I_a$-31 | 60 | — | — | — | — |
| $I_a$-32 | 20 | — | — | — | — |
| $I_a$-33 | 85 | — | — | — | — |
| $I_a$-34 | 15 | — | — | — | — |
| $I_b$-1 | 35 | — | — | — | — |
| $I_b$-2 | 15 | — | — | — | — |
| $I_b$-3 | 25 | — | — | — | — |
| $I_b$-4 | 75 | — | — | — | — |
| $I_b$-5 | 60 | — | — | — | — |
| $I_b$-6 | 35 | — | — | — | — |
| $I_b$-7 | 60 | — | — | — | — |
| $I_b$-8 | 30 | — | — | — | — |
| $I_b$-9 | 10 | — | — | — | — |

[a]not measured.

As seen from Table 2: most of the sulfonyl-structure-containing triazinone derivatives exhibit insecticidal activity against mosquito larvae. Especially, the compounds $I_a$-19, $I_a$-22, $I_a$-23 and $I_a$-26 exhibit relatively high insecticidal activity against mosquito larvae. At a concentration of 1 mg/kg, the compounds $I_a$-19, $I_a$-23 and $I_a$-26 exhibit insecticidal activity with mortalities of 60%, 30% and 20% respectively against mosquito larvae. Particularly, the compound $I_a$-22 exhibits insecticidal activity with a mortality of 40% against mosquito larvae at a concentration of 0.5 mg/kg.

Example 5: Test of Insecticidal Activity Against Cotton Bollworms, Maize Borers, and Armyworms, Through the Following Testing Procedure Test of Insecticidal Activity Against Cotton Bollworms Method of testing against cotton bollworms: the pesticide is mixed into the feedstuff, i.e., 3 mL prepared solution is added into about 27 g freshly prepared feedstuff; thus, required concentration is obtained by diluting by 10 times. After the mixture is mixed to a homogeneous state, the mixture is poured uniformly into a clean 24-orifice plate and cooled, then 24 third-instar cotton bollworms are inoculated into the 24-orifice plate; the result is checked after observation for 3-4 days.

Test of Insecticidal Activity Against Maize Borers

Method for testing against maize borers: a leaf immersion method is used, i.e., after the solution is prepared to a required concentration, leaves with diameters of about 5-6 cm are immersed in the solution for 5-6 s, taken out, and dried on absorbent papers, and then loaded into a specified culture dish; 10 third-instar larvae are inoculated into the culture dish, the culture dish is placed in an insectary at 27±1° C., and the result is checked after observation for 3-4 days.

Test of Insecticidal Activity Against Armyworms

Method of testing against armyworms: a leaf immersion method is used, i.e., after the solution is prepared to a required concentration, leaves with diameters of about 5-6 cm are immersed in the solution for 5-6 s, taken out, and dried on absorbent papers, and then loaded into a specified culture dish; 10 third-instar larvae are inoculated into the culture dish, the culture dish is placed in an insectary at 27±1° C., and the result is checked after observation for 3-4 days.

TABLE 3

Test Results of Insecticidal Activity of Pymetrozine and
the Sulfonyl-Structure-Containing Triazinone Derivatives
against Cotton Bollworms, Maize Borers, and Armyworms

| No. | Mortalities (%)/600 mg/kg | | |
|---|---|---|---|
| | Cotton bollworms | Maize borers | Armyworms |
| Pymetrozine | 20 | 35 | 50 |
| $I_a$-1 | 40 | 0 | 5 |
| $I_a$-2 | 5 | 15 | 10 |
| $I_a$-3 | 10 | 20 | 25 |
| $I_a$-4 | 0 | 5 | 5 |
| $I_a$-5 | 15 | 10 | 10 |
| $I_a$-6 | 30 | 40 | 50 |
| $I_a$-7 | 35 | 0 | 0 |
| $I_a$-8 | 0 | 0 | 10 |
| $I_a$-9 | 30 | 25 | 35 |
| $I_a$-10 | 50 | 40 | 40 |
| $I_a$-11 | 20 | 15 | 20 |
| $I_a$-12 | 30 | 10 | 15 |
| $I_a$-13 | 30 | 45 | 65 |
| $I_a$-14 | 0 | 0 | 0 |
| $I_a$-15 | 40 | 45 | 60 |
| $I_a$-16 | 10 | 15 | 10 |
| $I_a$-17 | 5 | 10 | 5 |
| $I_a$-18 | 0 | 25 | 50 |
| $I_a$-19 | 20 | 20 | 25 |
| $I_a$-20 | 20 | 50 | 65 |
| $I_a$-21 | 50 | 60 | 75 |
| $I_a$-22 | 100/80[a] | 100/65[a] | 100/70[a] |
| $I_a$-23 | 30 | 20 | 25 |
| $I_a$-24 | 50 | 5 | 5 |
| $I_a$-25 | 35 | 25 | 10 |
| $I_a$-26 | 0 | 40 | 45 |
| $I_a$-27 | 25 | 15 | 5 |
| $I_a$-28 | 10 | 5 | 5 |
| $I_a$-29 | 20 | 15 | 10 |
| $I_a$-30 | 25 | 15 | 20 |
| $I_a$-31 | 5 | 15 | 10 |
| $I_a$-32 | 0 | 0 | 5 |
| $I_a$-33 | 0 | 0 | 5 |
| $I_a$-34 | 10 | 10 | 15 |
| $I_b$-1 | 30 | 10 | 15 |
| $I_b$-2 | 25 | 5 | 5 |
| $I_b$-3 | 5 | 10 | 10 |
| $I_b$-4 | 45 | 10 | 15 |

TABLE 3-continued

Test Results of Insecticidal Activity of Pymetrozine and the Sulfonyl-Structure-Containing Triazinone Derivatives against Cotton Bollworms, Maize Borers, and Armyworms

| No. | Mortalities (%)/600 mg/kg | | |
|---|---|---|---|
|  | Cotton bollworms | Maize borers | Armyworms |
| $I_b$-5 | 20 | 25 | 40 |
| $I_b$-6 | 15 | 15 | 15 |
| $I_b$-7 | 40 | 15 | 20 |
| $I_b$-8 | 15 | 15 | 20 |
| $I_b$-9 | 5 | 10 | 15 |

$^a$mortality at a concentration of 200 mg/kg.

As seen from Table 3: most of the sulfonyl-structure-containing triazinone derivatives exhibit insecticidal activity against cotton bollworms, maize borers, and armyworms. Especially, the compound $I_a$-22, at a concentration of 200 mg/kg, exhibits insecticidal activity with mortalities of 80%, 65% and 70% respectively against cotton bollworms, maize borers, and armyworms.

Example 6: Test of Fungicidal Activity Against Fungi, Through the Following Testing Procedure Here, the test is described in an example of *Alternaria solani*; it can be replaced by other fungi.

In vitro testing method: *Alternaria solani* is inoculated to a PDA culture medium and cultured for 7 days, a fungus dish with a diameter of 4 cm is prepared on the periphery of the colony with a punch and inoculated to a PDA culture medium that contains pesticide at a concentration of 50 mg/kg and a PDA culture medium that doesn't contain the pesticide, and are cultured for 4 days respectively; then, the colony diameters are measured, and the inhibition percentages of the pesticides are calculated by comparing with the control sample.

TABLE 4

Test Results of Fungicidal Activity of the Sulfonyl-Structure-Containing Triazinone Derivatives

| No. | Fungicidal activity (%)/50 mg/kg | | | | | | |
|---|---|---|---|---|---|---|---|
|  | Cucumber fusarium wilt | Cercospora brown spot of peanut | Apple ring rot | Tomato early blight | Wheat head blight | Rice bakanae disease | Sclerotinia rot of colza |
| Carbendazim | <50 | <50 | <50 | <50 | 100 | <50 | 100 |
| Chlorothalonil | 100 | 73.3 | 100 | 73.3 | <50 | 100 | <50 |
| $I_a$-1 | 0.0 | 26.3 | 31.0 | 9.5 | 13.3 | 27.8 | 31.7 |
| $I_a$-2 | 5.0 | 15.8 | 20.7 | 33.3 | 20.0 | 50.0 | 56.7 |
| $I_a$-3 | 0.0 | 26.3 | 0.0 | 0.0 | 3.3 | 16.7 | 35.0 |
| $I_a$-4 | 0.0 | 15.8 | 31.0 | 14.3 | 6.7 | 38.9 | 48.3 |
| $I_a$-5 | 8.8 | 8.0 | 10.8 | 14.9 | 10.8 | 20.7 | 21.0 |
| $I_a$-6 | 20.6 | 13.0 | 39.2 | 12.9 | 10.9 | 12.5 | 31.6 |
| $I_a$-7 | 0.0 | 15.8 | 41.4 | 33.3 | 30.0 | 38.9 | 31.7 |
| $I_a$-8 | 20.5 | 19.2 | 0.0 | 20.0 | 33.3 | 7.4 | 16.7 |
| $I_a$-9 | 0.0 | 15.8 | 24.1 | 9.5 | 0.0 | 22.2 | 40.0 |
| $I_a$-10 | 5.9 | 4.0 | 10.8 | 9.0 | 13.5 | 13.8 | 21.0 |
| $I_a$-11 | 8.8 | 8.0 | 6.8 | 1.5 | 2.7 | 10.3 | 26.3 |
| $I_a$-12 | 25.0 | 42.1 | 41.4 | 33.3 | 13.3 | 27.8 | 70.0 |
| $I_a$-13 | 0.0 | 12.0 | 10.8 | 9.0 | 16.2 | 13.8 | 21.0 |
| $I_a$-14 | 8.8 | 12.0 | 33.8 | 13.4 | 16.2 | 10.3 | 15.8 |
| $I_a$-15 | 8.8 | 12.0 | 16.2 | 20.9 | 13.5 | 24.1 | 15.8 |
| $I_a$-16 | 2.9 | 8.0 | 17.6 | 13.4 | 10.8 | 27.6 | 15.8 |
| $I_a$-17 | 5.9 | 16.0 | 10.8 | 13.4 | 35.1 | 13.8 | 21.0 |
| $I_a$-18 | 14.7 | 12.0 | 8.1 | 11.9 | 2.7 | 20.7 | 21.0 |
| $I_a$-19 | 11.8 | 12.0 | 24.3 | 19.4 | 5.4 | 17.2 | 15.8 |
| $I_a$-20 | 0.0 | 12.0 | 4.1 | 16.4 | 5.4 | 10.3 | 15.8 |
| $I_a$-21 | 5.9 | 12.0 | 8.1 | 6.0 | 16.2 | 24.1 | 26.3 |
| $I_a$-22 | 14.7 | 16.0 | 37.8 | 6.0 | 16.2 | 17.2 | 21.0 |
| $I_a$-23 | 8.8 | 28.0 | 25.7 | 19.4 | 10.8 | 20.7 | 31.6 |
| $I_a$-24 | 0.0 | 15.8 | 13.8 | 23.8 | 6.7 | 27.8 | 40.0 |
| $I_a$-25 | 8.8 | 12.0 | 4.1 | 16.4 | 5.4 | 17.2 | 26.3 |
| $I_a$-26 | 2.9 | 12.0 | 23.0 | 13.4 | 13.5 | 17.2 | 15.8 |
| $I_a$-27 | 0.0 | 12.0 | 24.3 | 16.4 | 16.2 | 17.2 | 15.8 |
| $I_a$-28 | 0.0 | 12.0 | 0.0 | 23.9 | 8.1 | 17.2 | 15.8 |
| $I_a$-29 | 12.8 | 19.2 | 52.4 | 25.0 | 21.2 | 3.7 | 12.5 |
| $I_a$-30 | 23.1 | 19.2 | 23.8 | 20.0 | 12.1 | 14.8 | 12.5 |
| $I_a$-31 | 14.7 | 13.0 | 29.4 | 16.1 | 17.2 | 12.5 | 31.6 |
| $I_a$-32 | 8.8 | 26.1 | 43.1 | 16.1 | 12.5 | 18.8 | 15.8 |
| $I_a$-33 | 5.1 | 11.5 | 9.5 | 15.0 | 33.3 | 3.7 | 12.5 |
| $I_a$-34 | 8.8 | 13.0 | 39.2 | 16.1 | 10.9 | 12.5 | 6.6 |
| $I_b$-1 | 0.0 | 15.8 | 20.7 | 23.8 | 6.7 | 44.4 | 36.7 |
| $I_b$-2 | 10.0 | 15.8 | 58.6 | 33.3 | 13.3 | 27.8 | 48.3 |
| $I_b$-3 | 0.0 | 15.8 | 17.2 | 0.0 | 10.0 | 38.9 | 40.0 |
| $I_b$-4 | 20.0 | 15.8 | 27.6 | 19.0 | 3.3 | 50.0 | 43.3 |
| $I_b$-5 | 15.0 | 36.8 | 44.8 | 38.1 | 10.0 | 22.2 | 40.0 |
| $I_b$-6 | 0.0 | 15.8 | 27.6 | 23.8 | 13.3 | 22.2 | 15.0 |

TABLE 4-continued

Test Results of Fungicidal Activity of the Sulfonyl-
Structure-Containing Triazinone Derivatives

| | | | | | | | |
|---|---|---|---|---|---|---|---|
| $I_b$-7 | 5.0 | 21.1 | 0.0 | 23.8 | 23.3 | 44.4 | 30.0 |
| $I_b$-8 | 0.0 | 15.8 | 27.6 | 23.8 | 0.0 | 22.2 | 33.3 |
| $I_b$-9 | 7.7 | 19.2 | 21.4 | 25.0 | 21.2 | 0.0 | 12.5 |
| Pymetrozine | 5.0 | 15.8 | 27.6 | 23.8 | 13.3 | 33.3 | 31.7 |

| | Fungicidal activity (%)/50 mg/kg | | | | | |
|---|---|---|---|---|---|---|
| No. | Capsicum phytophthora blight | Wheat sheath blight | Corn southern leaf blight | Watermelon anthracnose | Potato late blight | Rice sheath blight |
| Carbendazim | <50 | 100 | 100 | 100 | 100 | 100 |
| Chlorothalonil | 100 | 100 | 91.3 | 91.3 | 86.4 | 100 |
| $I_a$-1 | 46.9 | 63.6 | 20.8 | 20.8 | 33.3 | 11.1 |
| $I_a$-2 | 36.7 | 63.6 | 29.2 | 33.3 | 22.2 | 34.9 |
| $I_a$-3 | 24.5 | 47.7 | 16.7 | 12.5 | 22.2 | 14.3 |
| $I_a$-4 | 46.9 | 70.5 | 33.3 | 25.0 | 40.7 | 34.9 |
| $I_a$-5 | 5.6 | 8.7 | 18.7 | 16.4 | 64.5 | 19.8 |
| $I_a$-6 | 18.8 | 30.9 | 7.7 | 12.5 | 3.1 | 11.6 |
| $I_a$-7 | 36.7 | 63.6 | 20.8 | 20.8 | 33.3 | 30.2 |
| $I_a$-8 | 26.9 | 30.2 | 8.3 | 0.0 | 28.6 | 17.9 |
| $I_a$-9 | 26.5 | 40.9 | 12.5 | 12.5 | 22.2 | 50.8 |
| $I_a$-10 | 9.4 | 14.3 | 37.5 | 39.2 | 18.7 | 17.4 |
| $I_a$-11 | 27.8 | 14.3 | 18.7 | 36.1 | 9.3 | 16.3 |
| $I_a$-12 | 40.8 | 72.7 | 33.3 | 33.3 | 29.6 | 27.0 |
| $I_a$-13 | 22.2 | 4.3 | 28.1 | 24.6 | 25.0 | 11.6 |
| $I_a$-14 | 13.9 | 21.7 | 9.3 | 26.2 | 3.1 | 11.6 |
| $I_a$-15 | 5.6 | 9.3 | 9.3 | 14.7 | 9.7 | 17.4 |
| $I_a$-16 | 13.9 | 14.3 | 0.0 | 8.2 | 3.1 | 11.6 |
| $I_a$-17 | 13.9 | 14.3 | 0.0 | 8.2 | 3.1 | 20.9 |
| $I_a$-18 | 5.6 | 4.3 | 3.1 | 14.7 | 18.7 | 22.1 |
| $I_a$-19 | 5.6 | 0.0 | 18.7 | 16.4 | 25.0 | 11.6 |
| $I_a$-20 | 0 | 17.4 | 3.1 | 13.1 | 18.7 | 9.3 |
| $I_a$-21 | 25.0 | 14.3 | 15.6 | 24.6 | 18.7 | 11.6 |
| $I_a$-22 | 27.8 | 8.7 | 3.1 | 56.3 | 25.0 | 23.2 |
| $I_a$-23 | 38.9 | 21.7 | 25.0 | 68.4 | 34.3 | 29.1 |
| $I_a$-24 | 24.5 | 52.3 | 25.0 | 12.5 | 22.2 | 50.8 |
| $I_a$-25 | 22.2 | 14.3 | 0.0 | 24.6 | 18.7 | 13.9 |
| $I_a$-26 | 27.8 | 0.0 | 6.3 | 34.4 | 34.3 | 20.9 |
| $I_a$-27 | 27.8 | 4.3 | 15.6 | 16.4 | 28.1 | 17.4 |
| $I_a$-28 | 25.0 | 8.7 | 18.7 | 0.0 | 0.0 | 17.4 |
| $I_a$-29 | 23.1 | 20.8 | 13.9 | 18.8 | 23.8 | 35.7 |
| $I_a$-30 | 11.5 | 7.5 | 19.4 | 25.0 | 14.3 | 14.3 |
| $I_a$-31 | 18.8 | 47.1 | 2.6 | 28.1 | 18.8 | 5.8 |
| $I_a$-32 | 9.4 | 30.9 | 7.7 | 18.8 | 18.8 | 10.5 |
| $I_a$-33 | 19.2 | 9.4 | 11.1 | 0.0 | 19.0 | 10.7 |
| $I_a$-34 | 18.8 | 36.8 | 10.3 | 18.8 | 3.1 | 4.7 |
| $I_b$-1 | 26.5 | 56.8 | 12.5 | 20.8 | 29.6 | 34.9 |
| $I_b$-2 | 38.8 | 61.4 | 16.7 | 12.5 | 18.5 | 27.0 |
| $I_b$-3 | 26.5 | 52.3 | 20.8 | 25.0 | 22.2 | 38.1 |
| $I_b$-4 | 34.7 | 65.5 | 20.8 | 29.2 | 33.3 | 27.0 |
| $I_b$-5 | 42.9 | 68.2 | 25.0 | 20.8 | 22.2 | 27.0 |
| $I_b$-6 | 26.5 | 56.8 | 16.7 | 29.2 | 22.2 | 50.8 |
| $I_b$-7 | 36.7 | 59.1 | 12.5 | 20.8 | 25.9 | 27.0 |
| $I_b$-8 | 20.4 | 45.5 | 16.7 | 12.5 | 29.6 | 27.0 |
| $I_b$-9 | 11.5 | 15.1 | 5.6 | 3.1 | 14.3 | 26.8 |
| Pymetrozine | 36.7 | 63.6 | 16.7 | 16.7 | 22.2 | 19.0 |

As seen from Table 4: most of the sulfonyl-structure-containing triazinone derivatives exhibit satisfactory fungicidal activity against 13 strains of pathogenic fungi; especially, the compounds $I_a$-4, $I_a$-12 and $I_b$-5 exhibit outstanding fungicidal activity against a variety of pathogenic fungi at a concentration of 50 mg/kg.

The invention claimed is:

1. A sulfonyl-structure-containing triazinone derivative, which is a compound represented by formula ($I_a$) or formula ($I_b$):

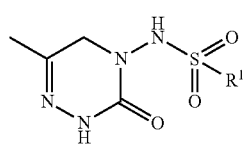

formula ($I_a$)

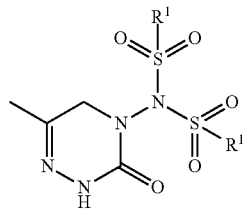

formula ($I_b$)

wherein $R^1$ is C1-C12 alkyl, C3-C6 cycloalkyl, substituted or unsubstituted phenyl, substituted or unsubstituted naphthyl, substituted or unsubstituted benzyl, substituted or unsubstituted phenethyl, substituted or unsubstituted phenylpropyl, substituted or unsubstituted phenylbutyl, nitrogen-containing heterocycle containing 1-10 carbon atoms, oxygen-containing heterocycle containing 1-10 carbon atoms, or sulfur-containing heterocycle containing 1-10 carbon atoms; wherein the substituents of the substituted phenyl, the substituted naphthyl, the substituted benzyl, the substituted phenethyl, substituted phenylpropyl, and the substituted phenylbutyl are one or more substituents respectively and are independently selected from the group consisting of hydroxyl, halogen, cyano, nitro, ester, trifluoromethyl, trifluoromethoxy, amido, C1-C6 alkyl, C1-C6 alkoxy, carbonyloxy substituted by C1-C4 alkyl, and carbonyloxy substituted by C1-C4 alkoxy.

2. The triazinone derivative according to claim 1, wherein $R^1$ is C1-C8 alkyl, C3-C6 cycloalkyl, substituted or unsubstituted phenyl, substituted or unsubstituted naphthyl, substituted or unsubstituted benzyl, substituted or unsubstituted phenethyl, substituted or unsubstituted phenylpropyl, substituted or unsubstituted phenylbutyl, nitrogen-containing heterocycle containing 2-8 carbon atoms, oxygen-containing heterocycle containing 2-8 carbon atoms, or sulfur-containing heterocycle containing 2-8 carbon atoms; wherein the substituents of the substituted phenyl, the substituted naphthyl, the substituted benzyl, the substituted phenethyl, the substituted phenylpropyl, and the substituted phenylbutyl are one or more substituents respectively and are independently selected from the group consisting of hydroxyl, F, Cl, Br, I, cyano, nitro, —COOCH$_3$, —COOCH$_2$CH$_3$, trifluoromethyl, trifluoromethoxy, —NH—CO—CH$_3$, —NH—CO—CH$_2$CH$_3$, methyl, ethyl, n-propyl, isopropyl, n-butyl, isobutyl, sec-butyl, tert-butyl, n-pentyl, methoxy, ethoxy, n-propoxy, isopropoxy, n-butoxy, isobutoxy, sec-butoxy, tert-butoxy, n-pentyloxy, C1-C5 alkyl, C1-C5 alkoxy, —O—CO—CH$_3$, —O—CO—CH$_2$CH$_3$, —O—CO—O—CH$_3$, and —O—CO—O—CH$_2$CH$_3$.

3. The triazinone derivative according to claim 1, wherein the compound represented by formula ($I_a$) or formula ($I_b$) is at least one of the compounds represented by the following formulae:

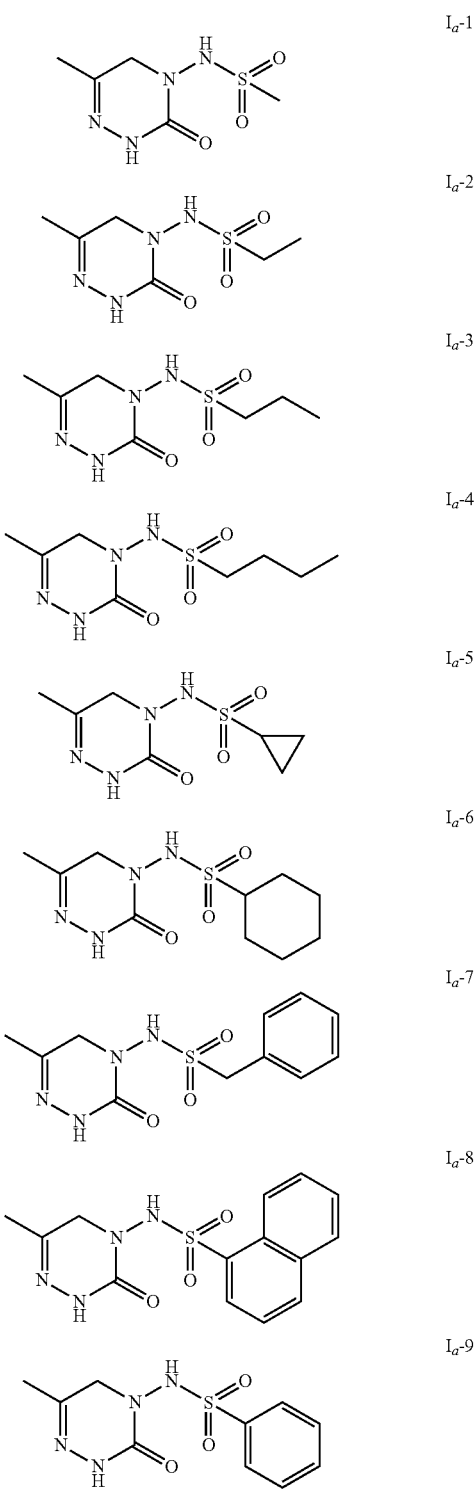

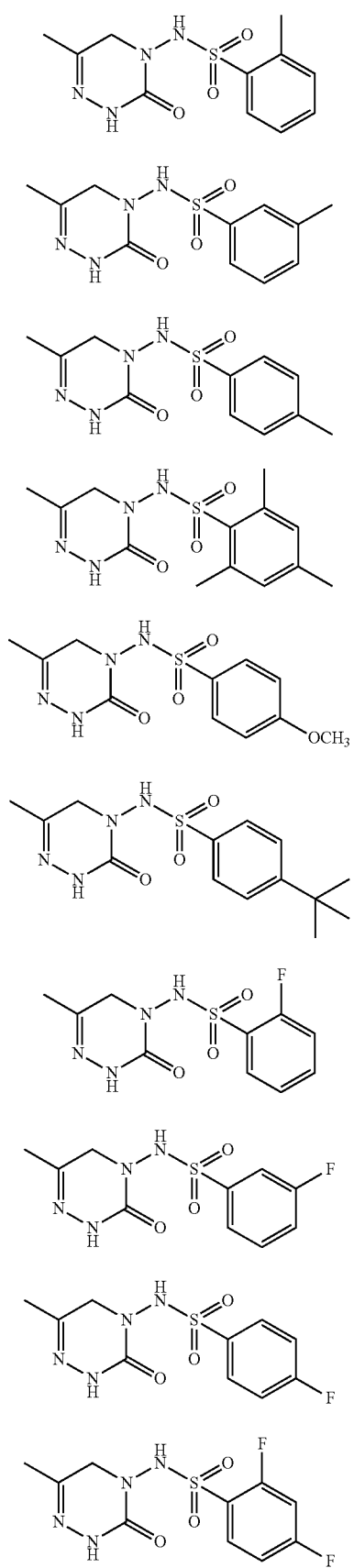
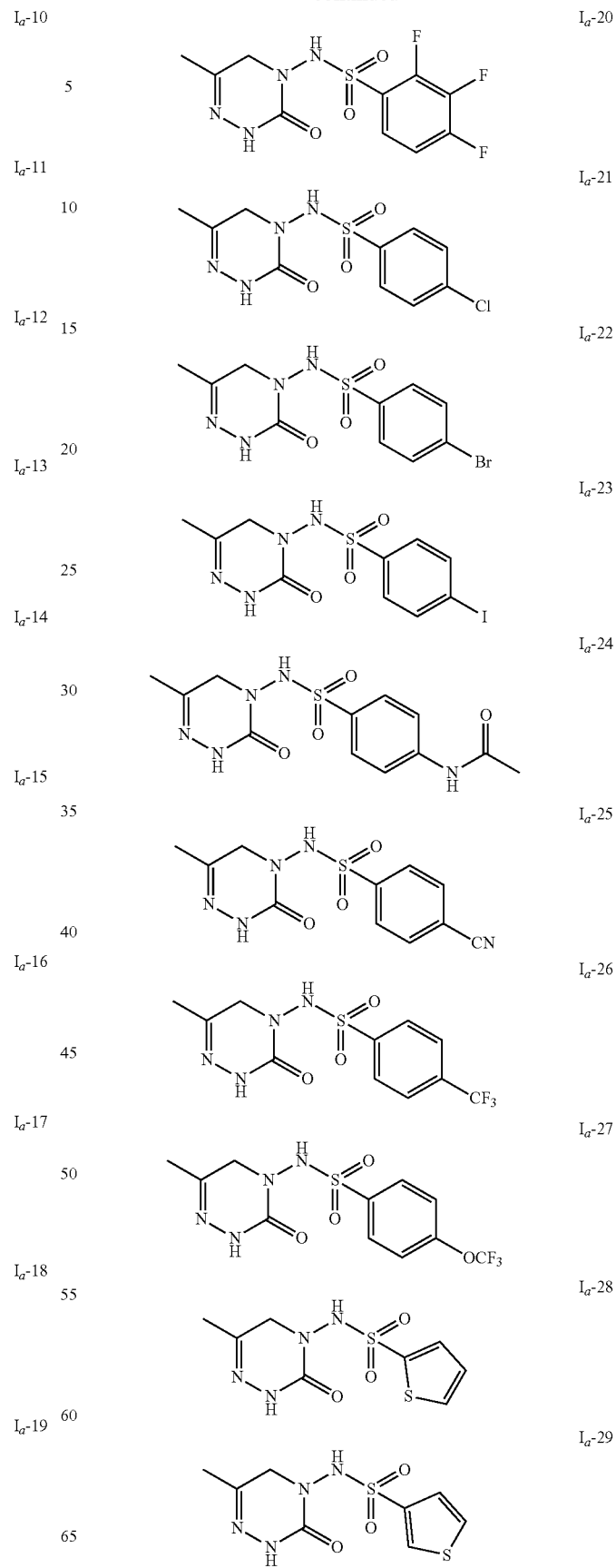

-continued
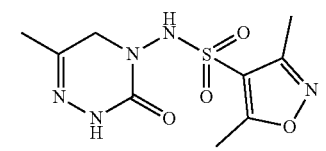
I<sub>a</sub>-30
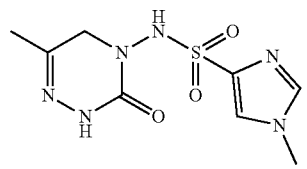
I<sub>a</sub>-31
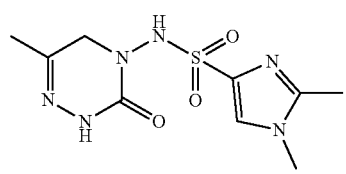
I<sub>a</sub>-32
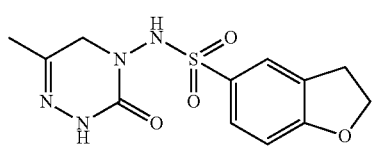
I<sub>a</sub>-33
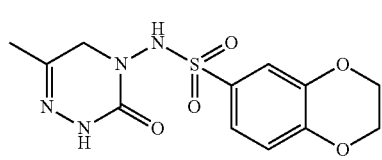
I<sub>a</sub>-34
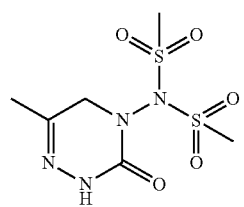
I<sub>b</sub>-1
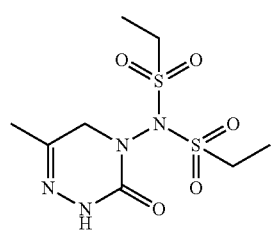
I<sub>b</sub>-2
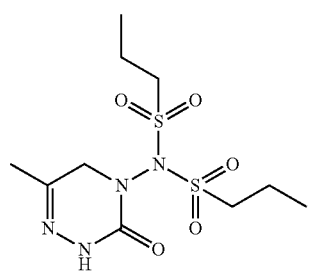
I<sub>b</sub>-3
-continued
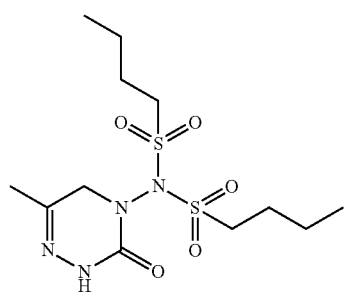
I<sub>b</sub>-4
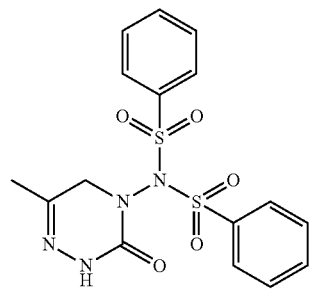
I<sub>b</sub>-5
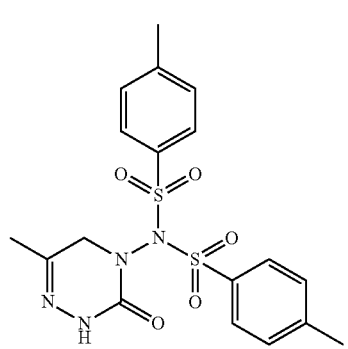
I<sub>b</sub>-6
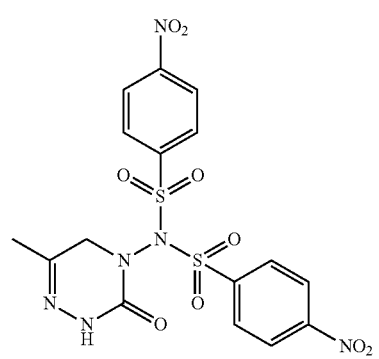
I<sub>b</sub>-7

-continued

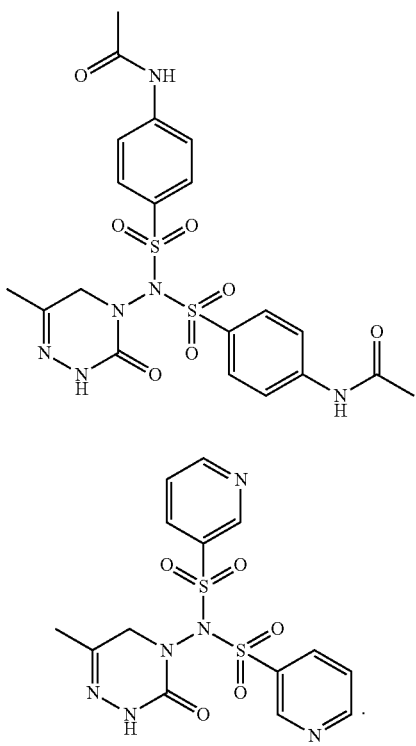

I$_b$-8

I$_b$-9

4. A method for preparing the triazinone derivative according to claim 1, comprising: reacting by substitution reaction an amino-triazinone represented by formula (II) and sulfonyl chloride compound represented by formula (III) in an organic solvent in the presence of an acid binding agent to obtain a compound represented by formula (I$_a$) or formula (I$_b$);

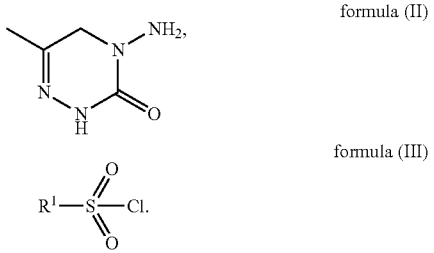

formula (II)

formula (III)

5. The method according to claim 4,
when the obtained compound is represented by formula (I$_a$), the molar ratio of the amino-triazinone represented by formula (II) to the sulfonyl chloride compound represented by formula (III) is 1:1.2 to 1:0.8; and
when the obtained compound is represented by formula (I$_b$), the molar ratio of the amino-triazinone represented by formula (II) to the sulfonyl chloride compound represented by formula (III) is 1:2.5 to 1:1.8;
wherein the acid binding agent is at least one of the agents selected from the group consisting of sodium carbonate, potassium carbonate, cesium carbonate, triethylamine, and pyridine; the organic solvent is at least one of the solvents selected from the group consisting of methanol, ethanol, pyridine, N,N-dimethyl formamide and dimethyl sulfoxide; and the organic solvent is dosed so that the concentration of the amino-triazinone represented by formula (II) is 0.05-0.5 mmol/mL.

6. The method according to claim 4, wherein the conditions of the substitution reaction include: temperature: 15-40° C.; time: 4-12 h.

7. A method of insect and/or fungus killing comprising exposing the insect and/or fungus to the triazinone derivative according to claim 1.

8. The method according to claim 7, wherein the insect is at least one of aphides, mosquito larvae, cotton bollworms, maize borers, and armyworms; and the fungus is at least one of the pathogenic fungi that causes tomato early blight, wheat head blight, potato late blight, *Capsicum phytophthora* blight, *Sclerotinia* rot of colza, cucumber gray mold, rice sheath blight, cucumber *Fusarium* wilt, *Cercospora* brown spot of peanut, apple ring rot, wheat sheath blight, corn southern leaf blight, watermelon anthracnose, and rice bakanae disease.

9. The method according to claim 4,
when the obtained compound is represented by formula (I$_a$), the molar ratio of the amino-triazinone represented by formula (II) to the sulfonyl chloride compound represented by formula (III) is 1:1.1 to 1:1; and
when the obtained compound is represented by formula (I$_b$), the molar ratio of the amino-triazinone represented by formula (II) to the sulfonyl chloride compound represented by formula (III) is 1:2.4 to 1:2;
wherein the acid binding agent is at least one of the agents selected from the group consisting of sodium carbonate, potassium carbonate, cesium carbonate, triethylamine, and pyridine; the organic solvent is at least one of the solvents selected from the group consisting of methanol, ethanol, pyridine, N,N-dimethyl formamide and dimethyl sulfoxide; and the organic solvent is dosed so that the concentration of the amino-triazinone represented by formula (II) is 0.05-0.5 mmol/mL.

* * * * *